US012590092B2

(12) United States Patent
Von Itzstein et al.

(10) Patent No.: US 12,590,092 B2
(45) Date of Patent: Mar. 31, 2026

(54) ANTIVIRAL AGENTS AND USES THEREOF

(71) Applicant: GRIFFITH UNIVERSITY, Nathan (AU)

(72) Inventors: Mark Von Itzstein, Palm Beach (AU); Ibrahim El-Deeb, Runaway Bay (AU); Patrice Guillon, Southport (AU); Larissa Heilig, Burleigh Waters (AU)

(73) Assignee: GRIFFITH UNIVERSITY, Nathan (AU)

( * ) Notice: Subject to any disclaimer, the term of this patent is extended or adjusted under 35 U.S.C. 154(b) by 367 days.

(21) Appl. No.: 18/263,481

(22) PCT Filed: Jan. 28, 2022

(86) PCT No.: PCT/AU2022/050046
§ 371 (c)(1),
(2) Date: Jul. 28, 2023

(87) PCT Pub. No.: WO2022/160015
PCT Pub. Date: Aug. 4, 2022

(65) Prior Publication Data

US 2024/0109886 A1 Apr. 4, 2024

(30) Foreign Application Priority Data

Jan. 29, 2021 (AU) ................................ 2021900202

(51) Int. Cl.
*C07D 471/04* (2006.01)
*A61P 31/16* (2006.01)
*C07D 487/04* (2006.01)
*C07D 495/04* (2006.01)

(52) U.S. Cl.
CPC ............ *C07D 471/04* (2013.01); *A61P 31/16* (2018.01); *C07D 487/04* (2013.01); *C07D 495/04* (2013.01)

(58) Field of Classification Search
CPC ..... A61P 31/16; C07D 471/04; C07D 487/04; C07D 495/04; C07D 487/14; C07D 491/048
See application file for complete search history.

(56) References Cited

U.S. PATENT DOCUMENTS 5,639,786 A 6/1997 Von Itzstein et al.

FOREIGN PATENT DOCUMENTS

WO 2002/076971 A1 10/2002
WO WO 2016/033660 * 3/2016 .......... C07D 405/04
WO WO 2016/033660 A1 3/2016
WO WO 2021/016670 A1 2/2021

OTHER PUBLICATIONS

Adams et al., “Phenix: A Comprehensive Python-based System for Macromolecular Structure Solution,” Acta. Crystallogr. D. Biol. Crystallogr., 66(Pt 2): 213-221 (2010).
Bailly et al., “A Dual Drug Regimen Synergistically Blocks Human Parainfluenza Virus Infection,” Sci. Rep., 6: 24138 (2016).
Chen et al., “MolProbity: All-Atom Structure Validation for Macromolecular Crystallography,” Acta. Crystallogr. D. Biol. Crystallogr., 66(Pt 1): 12-21 (2010).
Dirr et al., “The Catalytic Mechanism of Human Parainfluenza Virus Type 3 Haemagglutinin-Neuraminidase Revealed,” Angew. Chem. Int. Ed., 54(10): 2936-2940 (2015).
Dirr et al., “The Impact of the Butterfly Effect on Human Parainfluenza Virus Haemagglutinin-neuraminidase Inhibitor Design,” Sci. Rep., 7(1): 4507 (2017).
El-Deeb et al., “Exploring Human Parainfluenza Virus Type-1 Hemagglutinin-Neuraminidase as a Target for Inhibitor Discovery,” J. Med. Chem., 57(18): 7613-7623 (2014).
(Continued)

*Primary Examiner* — Joseph K Mckane
*Assistant Examiner* — David M Shim
(74) *Attorney, Agent, or Firm* — Leydig, Voit & Mayer, Ltd.

(57) ABSTRACT

The present invention relates to a compound of Formula (I), or a pharmaceutically acceptable salt thereof:

Formula (I)

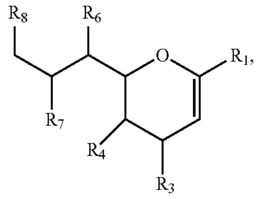

and to pharmaceutical compositions comprising the compound. In Formula (I), $R_3$ is selected from the group consisting of:

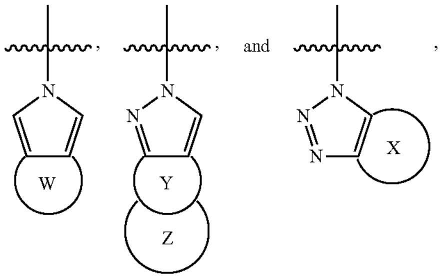

wherein rings W, X, Y and Z may relate to various heterocyclic, heteroaryl, cycloalkyl, cycloalkenyl, and/or aryl rings. The present invention also relates to uses of the compounds in treating a disease, disorder or condition caused by viral infection.

21 Claims, No Drawings

(56) References Cited

OTHER PUBLICATIONS

El-Deeb et al., "Exploring Inhibitor Structural Features Required to Engage the 216-loop of Human Parainfluenza Virus Type-3 Hemagglutinin-Neuraminidase," Med. Chem. Commun., 8(1): 130-134 (2017).
Emsley et al., "Coot: Model-Building Tools for Molecular Graphics," Acta. Crystallogr. D. Biol. Crystallogr., 60 (Pt 12 Pt 1): 2126-2132 (2004).
Eveno et al., "Targeting Human Parainfluenza Virus Type-1 Haemagglutinin-Neuraminidase with Mechanism-Based Inhibitors," Viruses, 11(5): 417 (2019).
Guillon et al., "Structure-Guided Discovery of Potent and Dual-Acting Human Parainfluenza Virus Haemagglutinin-Neuraminidase Inhibitors," Nat. Commun., 5: 5268 (2014).
Kabsch, "XDS," Acta. Crystallogr. D. Biol. Crystallogr., 66(Pt 2): 125-132 (2010).
Li et al., "Syntheses of Triazole-Modified Zanamivir Analogues via Click Chemistry and Anti-AIV Activities," Bioorg. Med. Chem. Lett., 16(19): 5009-5013 (2006).
Lu et al., "Synthesis of C-4 and C-7 Triazole Analgos of Zanamivir as Multivalent Sialic Acid Containing Scaffolds," Carbohydr. Res., 342(12-13): 1636-1650 (2007).
Potterton et al., "CCP4i2: The New Graphical User Interface to the CCP4 Program Suite," Acta. Crystallogr. D. Struct. Biol., 74(Pt 2): 68-84 (2018).
Von Itzstein et al., "A Convenient Method for the Introduction of Nitrogen and Sulfur at C-4 on a Sialic Acid Analogue," Carbohydr. Res., 244(1): 181-185 (1993).
European Patent Office, Extended European Search Report in European Patent Application No. 22744942.8 (Nov. 26, 2024).
Australian Patent Office, International Search Report in International Patent Application No. PCT/AU2022/050046 (Apr. 11, 2022).

* cited by examiner

ANTIVIRAL AGENTS AND USES THEREOF

FIELD OF THE INVENTION

The invention relates to the field of medical treatment. More particularly, this invention relates to novel antiviral agents and their use in treating a disease or condition caused by a viral infection.

BACKGROUND TO THE INVENTION

Any reference to background art herein is not to be construed as an admission that such art constitutes common general knowledge in Australia or elsewhere.

Viruses are responsible for a wide range of mammalian disease which represents a great cost to society. The effects of viral infection can range from common flu symptoms to serious respiratory problems and can result in death, particularly amongst the young, elderly and immunocompromised members of the community.

Viruses of the family Orthomyxoviridae, including influenza virus types A, B and C, and the family Paramyxoviridae are the pathogenic organisms responsible for a significant number of human infections annually.

Taking the family Paramyxoviridae as one example, human parainfluenza viruses types 1 and 3 (hPIV-1 and 3) are a leading cause of upper and lower respiratory tract disease in infants and young children and impact the elderly and immunocompromised. Significantly, it is estimated that in the United States alone up to five million lower respiratory tract infections occur each year in children under 5 years old, and hPIV has been isolated in approximately one third of these cases. hPIV infections are frequently reported in transplant patients, with the mortality rate as high as 30% in hematopoietic stem cell transplant patients. There are currently neither vaccines nor specific antiviral therapy to prevent or treat hPIV infections respectively, despite continuing efforts. Some of the more recent approaches have focussed on an entry blockade and the triggering of premature virus fusion by a small molecule.

An initial interaction of the parainfluenza virus with the host cell is through its surface glycoprotein, haemagglutinin-neuraminidase (HN) and involves recognition of N-acetylneuraminic acid-containing glycoconjugates. The parainfluenza virus HN is a multifunctional protein that encompasses the functions of receptor binding (for cell adhesion) and receptor destruction (facilitating virus release), not only within the one protein, but apparently in a single binding site. In addition, the HN is involved in activation of the viral surface fusion (F) protein necessary to initiate infection of the target host cell. Inhibition of haemagglutinin-neuraminidase may therefore provide a target for antivirals.

Certain antiviral compounds have been disclosed in the present Applicant's earlier filed International Application published as WO 2016/033660 as modulators of viral haemagglutinin-neuraminidase functions. While suitable for their purpose, the publication provides limited discussion in terms of the variability which is tolerated at certain key positions.

SUMMARY OF INVENTION

According to a first aspect of the invention, there is provided a compound of formula (I), or a pharmaceutically acceptable salt thereof:

Formula (I)

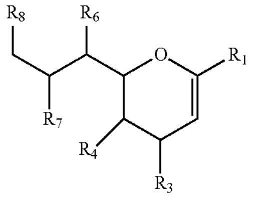

wherein, $R_1$ is selected from the group consisting of COOH, or a salt thereof, $C(O)NR_9R_{10}$, and $C(O)OR_{11}$ wherein $R_9$, $R_{10}$ and $R_{11}$ are independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl and optionally substituted heterocyclyl;

$R_3$ is selected from the group consisting of:

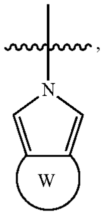
,
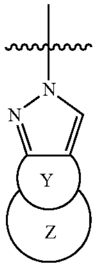
and
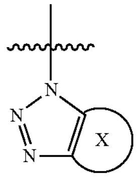

wherein ring W, together with the carbon atoms to which it is attached, form an optionally substituted monocyclic heterocyclic ring, an optionally substituted monocyclic heteroaryl ring, an optionally substituted fused bicyclic heterocyclic ring or an optionally substituted fused bicyclic heteroaryl ring;

wherein:

(i) ring Y, together with the carbon atoms to which it is attached, form an optionally substituted monocyclic heterocyclic ring or an optionally substituted monocyclic heteroaryl ring; and ring Z, together with two ring atoms of ring Y, form an optionally substituted monocyclic heterocyclic ring, an optionally substituted monocyclic heteroaryl ring, an optionally substituted monocyclic cycloalkyl ring, an optionally substituted monocyclic cycloalkenyl ring or an optionally substituted monocyclic aryl ring, or may be absent; or (ii) ring Y, together with the carbon atoms to which it is attached, form an optionally substituted phenyl ring; and ring Z, together with two ring atoms of ring Y, form an optionally substituted monocyclic heterocyclic ring or an optionally substituted monocyclic heteroaryl ring, wherein said monocyclic heterocyclic or heteroaryl ring comprises at least one N ring atom;

wherein ring X, together with the carbon atoms to which it is attached, form:

(a) an optionally substituted monocyclic heterocyclic ring, an optionally substituted monocyclic heteroaryl ring, an optionally substituted fused bicyclic heterocyclic ring or an optionally substituted fused bicyclic heteroaryl ring; or (b) a phenyl ring substituted by a heterocyclic or heteroaryl ring, wherein said phenyl, heterocyclic and/or heteroaryl ring are optionally substituted;

$R_4$ is selected from the group consisting of sulfonamide, urea and $NHC(O)R_{17}$ wherein $R_{17}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_3$-$C_6$ cycloalkenyl, all of which may be optionally substituted;

$R_6$, $R_7$ and $R_8$ are independently selected from the group consisting of H, OH, protected OH, $R_{19}O$—$R_{19}$, $NR_{18}R_{18}'$, —$C(O)R_{18}$, —$C(S)R_{18}$, —$O(C(O)R_{18}$, —$C(O)OR_{18}$, —$NH(C{=}O)R_{18}$, —$C({=}O)NR_{18}R_{18}'$, and $S(O)_nR_{18}$, wherein n=0-2 and each $R_{18}$ and $R_{18}'$ are independently selected from hydrogen, $R_{19}$ and optionally substituted $C_1$-$C_9$ alkanoyl, as appropriate; wherein each $R_{19}$ is independently selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, cycloalkyl, cycloalkenyl, heteroaryl and heterocyclyl, wherein any $R_{19}$ group is optionally substituted.

According to one embodiment of the first aspect of the invention, there is provided a compound of formula (I), or a pharmaceutically acceptable salt thereof:

Formula (I)

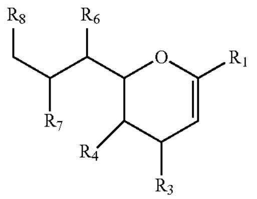

wherein, $R_1$ is selected from the group consisting of COOH, or a salt thereof, $C(O)NR_9R_{10}$, and $C(O)OR_{11}$ wherein R9, $R_{10}$ and $R_{11}$ are independently selected from the group consisting of hydrogen, $C_1$-$C_6$ alkyl, $C_2$-$C_6$ alkenyl, $C_2$-$C_6$ alkynyl, aryl, heteroaryl and heterocyclyl; wherein said $C_1$-$C_6$ alkyl, $C_2$-$C_6$ alkenyl, $C_2$-$C_6$ alkynyl, aryl, heteroaryl and heterocyclyl are optionally substituted by one or more $R_{50}$; wherein $R_{50}$ is selected from the group consisting of: $R_{53}$, —O—$R_{53}$, —S—$R_{53}$, —C(O)—$R_{53}$, —C(S)—$R_{53}$, —C(O)—O—$R_{53}$, —O—C(O)—$R_{53}$, —O—C(S)—$R_{53}$, —C(S)—O—$R_{53}$, CN, OH, oxo, $NR_{51}R_{51}'$, Cl, F, Br, I, aryl optionally substituted by at least one $R_{52}$ and heterocyclyl optionally substituted by at least one $R_{52}$; wherein $R_{51}$ and $R_{51}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C=O—$C_1$-$C_9$ alkyl, $SO_2$-$C_1$-$C_9$ alkyl and C=O—NH—$C_1$-$C_9$ alkyl; wherein $R_{52}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{51}R_{51}'$, Cl, F, Br and I; wherein $R_{53}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl;

$R_3$ is selected from the group consisting of:

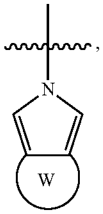, 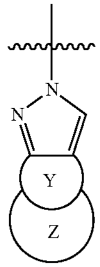 and 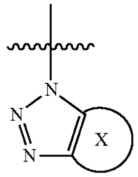

wherein ring W, together with the carbon atoms to which it is attached, form a monocyclic heterocyclic ring optionally substituted by one or more $R_{55}$, a monocyclic heteroaryl ring optionally substituted by one or more $R_{55}$, a fused bicyclic heterocyclic ring optionally substituted by one or more $R_{55}$, or a fused bicyclic heteroaryl ring optionally substituted by one or more $R_{55}$; wherein $R_{55}$ is selected from the group consisting of: $R_{58}$, —O—$R_{58}$, —S—$R_{58}$, —C(O)—$R_{58}$, —C(S)—$R_{58}$, —C(O)—O—$R_{58}$, —O—C(O)—$R_{58}$, —O—C(S)—$R_{58}$, —C(S)—O—$R_{58}$, CN, OH, oxo, $NR_{56}R_{56}'$, Cl, F, Br, I, aryl optionally substituted by at least one $R_{57}$ and heterocyclyl optionally substituted by at least one $R_{57}$; wherein $R_{56}$ and $R_{56}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C=O—$C_1$-$C_9$ alkyl, aryl, $SO_2$-$C_1$-$C_9$ alkyl and C=O—NH—$C_1$-$C_9$ alkyl; wherein $R_{57}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{56}R_{56}'$, Cl, F, Br and I; wherein $R_{58}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, heteroaryl, heterocyclyl, cycloalkyl and cycloalkenyl;

wherein:

(i) ring Y, together with the carbon atoms to which it is attached, form a monocyclic heterocyclic ring optionally substituted by one or more $R_{60}$ or a monocyclic heteroaryl ring optionally substituted by one or more $R_{60}$; and ring Z, together with two ring atoms of ring Y, form a monocyclic heterocyclic ring optionally substituted by one or more $R_{60}$, a monocyclic heteroaryl ring optionally substituted by one or more $R_{60}$, a monocyclic cycloalkyl ring optionally substituted by one or more $R_{60}$, a monocyclic cycloalkenyl ring optionally substituted by one or more $R_{60}$, or a monocyclic aryl ring optionally substituted by one or more $R_{60}$, or may be absent; wherein $R_{60}$ is selected from the group consisting of: $R_{63}$, —O—$R_{63}$, —S—$R_{63}$, —C(O)—$R_{63}$, —C(S)—$R_{63}$, —C(O)—O—$R_{63}$, —C(O)—OH (or a salt thereof), —O—C(O)—$R_{63}$, —O—C(S)—$R_{63}$, —C(S)—O—$R_{63}$, CN, OH, oxo, $NR_{61}R_{61}'$, Cl, F, Br, I, aryl optionally substituted by at least one $R_{62}$ and heterocyclyl optionally substituted by at least one $R_{62}$; wherein $R_{61}$ and $R_{61}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C=O—$C_1$-$C_9$ alkyl, aryl, $SO_2$—$C_1$-$C_9$ alkyl and C=O—NH—$C_1$-$C_9$ alkyl; wherein $R_{62}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{61}R_{61}'$, Cl, F, Br and I; wherein $R_{63}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$ -$C_6$ haloalkynyl, aryl, heteroaryl, heterocyclyl, cycloalkyl and cycloalkenyl; or (ii) ring Y, together with the carbon atoms to which it is attached, form a phenyl ring optionally substituted by one or more $R_{65}$; and ring Z, together with two ring atoms of ring Y, form a monocyclic heterocyclic ring optionally substituted by one or more $R_{65}$, or a monocyclic heteroaryl ring optionally substituted by one or more $R_{65}$, wherein said monocyclic heterocyclic or heteroaryl ring comprises at least one N ring atom;

wherein $R_{65}$ is selected from the group consisting of: $R_{68}$, —O —$R_{68}$, —S—$R_{68}$, —C(O)—$R_{68}$, —C(S)—$R_{68}$, —C(O)—O—$R_{68}$, —O—C(O)—$R_{68}$, —O—C(S)—$R_{68}$, —C(S)—O—$R_{68}$, CN, OH, oxo, $NR_{66}R_{66}'$, Cl, F, Br, I, aryl optionally substituted by at least one $R_{67}$ and heterocyclyl optionally substituted by at least one $R_{67}$; wherein $R_{66}$ and $R_{66}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, aryl, $SO_2$-$C_1$-$C_9$ alkyl and C═O—NH—$C_1$-$C_9$ alkyl; wherein $R_{67}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{66}R_{66}'$, Cl, F, Br and I; wherein $R_{68}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, heteroaryl, heterocyclyl, cycloalkyl and cycloalkenyl;

wherein ring X, together with the carbon atoms to which it is attached, form:

(a) a monocyclic heterocyclic ring optionally substituted by one or more $R_{70}$, a monocyclic heteroaryl ring optionally substituted by one or more $R_{70}$, a fused bicyclic heterocyclic ring optionally substituted by one or more $R_{70}$, or a fused bicyclic heteroaryl ring optionally substituted by one or more $R_{70}$; or (b) a phenyl ring substituted by a heterocyclic or heteroaryl ring, wherein said phenyl, heterocyclic and/or heteroaryl ring are optionally substituted by one or more $R_{70}$; wherein $R_{70}$ is selected from the group consisting of: $R_{73}$, —O—$R_{73}$, —S—$R_{73}$, —C(O)—$R_{73}$, —C(S)—$R_{73}$, —C(O)—O—$R_{73}$, —O—C(O)—$R_{73}$, —O—C(S)—$R_{73}$, —C(S)—O—$R_{73}$, CN, OH, oxo, $NR_{71}R_{71}'$, Cl, F, Br, I, aryl optionally substituted by at least one $R_{72}$ and heterocyclyl optionally substituted by at least one $R_{72}$; wherein $R_{71}$ and $R_{71}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$—$C_9$ alkyl, aryl, $SO_2$—$C_1$-$C_9$ alkyl and C=O—NH—$C_1$-$C_9$ alkyl; wherein $R_{72}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{66}R_{66}'$, Cl, F, Br and I; wherein $R_{73}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, heteroaryl, heterocyclyl, cycloalkyl and cycloalkenyl;

$R_4$ is selected from the group consisting of sulfonamide, urea and $NHC(O)R_{17}$ wherein $R_{17}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl and $C_3$-$C_6$ cycloalkenyl; wherein said $R_{17}$ groups may be optionally substituted by one or more $R_{75}$; wherein $R_{75}$ is selected from the group consisting of: $R_{78}$, —O—$R_{78}$, —S—$R_{78}$, —C(O)—$R_{78}$, —C(S)—$R_{78}$, —C(O)—O—$R_{78}$, —O—C(O)—$R_{78}$, —O—C(S)—$R_{78}$, —C(S)—O—$R_{78}$, CN, OH, oxo, $NR_{76}R_{76}'$, Cl, F, Br, I, aryl optionally substituted by at least one $R_{77}$ and heterocyclyl optionally substituted by at least one $R_{77}$; wherein $R_{76}$ and $R_{76}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$—$C_1$-$C_9$ alkyl and C═O—NH—$C_1$-$C_9$ alkyl; wherein $R_{77}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{76}R_{76}'$, Cl, F, Br and I; wherein $R_{78}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl;

$R_6$, $R_7$ and $R_8$ are independently selected from the group consisting of H, OH, protected OH, $R_{19}$, O—$R_{19}$, $NR_{18}R_{18}'$, —C(O)$R_{18}$, —C(S)$R_{18}$, —OC(O)$R_{18}$, —C(O)O$R_{18}$, —NH(C═O)$R_{18}$, —C(═O)$NR_{18}R_{18}'$, and $S(O)_n$ $R_{18}$, wherein n=0-2 and each $R_{18}$ and $R_{18}'$ are independently selected from hydrogen, $R_{19}$ optionally substituted by one or more $R_{80}$ and $C_1$-$C_9$ alkanoyl optionally substituted by one or more $R_{80}$; wherein each $R_{19}$ is independently selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, cycloalkyl, cycloalkenyl, heteroaryl and heterocyclyl; wherein $R_{80}$ is selected from the group consisting of: $R_{83}$, —O—$R_{83}$, —S—$R_{83}$, —C(O)—$R_{83}$, —C(S)—$R_{83}$, —C(O)—O—$R_{83}$, —O—C(O)—$R_{83}$, —O—C(S)—$R_{83}$, —C(S)—O—$R_{83}$, CN, OH, oxo, $NR_{81}R_{81}'$, Cl, F, Br, I, aryl optionally substituted by at least one $R_{83}$ and heterocyclyl optionally substituted by at least one $R_{82}$; wherein $R_{81}$ and $R_{81}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-C9 haloalkynyl, C═O—$C_1$-$C_9$ alkyl, $SO_2$—$C_1$-C9 alkyl and C═O—NH-$C_1$-$C_9$ alkyl; wherein $R_{82}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{76}R_{76}'$, Cl, F, Br and I; wherein $R_{83}$ is selected from the group consisting of: $C_1$-$C_6$ alkyl, $C_1$-$C_6$ haloalkyl, $C_2$-$C_6$ alkenyl, $C_2$-$C_6$ haloalkenyl, C2-$C_6$ alkynyl, and $C_2$-$C_6$ haloalkynyl.

In one embodiment of the first aspect, the compound of formula (I) is a compound of formula (II):

Formula (II)

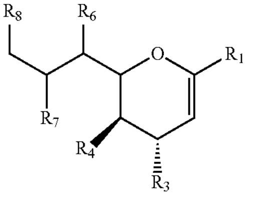

wherein, $R_1$, $R_3$, $R_4$, $R_6$, $R_7$ and $R_8$ are as described above.

In one embodiment of the first aspect, the compound of formula (I) is a compound of formula (III):

Formula (III)

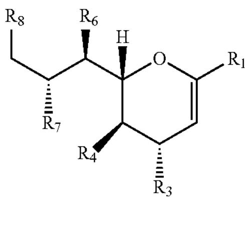

wherein, $R_1$, $R_3$, $R_4$, $R_6$, $R_7$ and $R_8$ are as described above.

The present invention is predicated, at least in part, on the finding that certain neuraminic acid derivatives with modifications at key positions, including the C-4 position of the ring, display useful efficacy in the treatment of diseases caused by viral respiratory infection. Particularly, the compounds of the invention are useful in the inhibition of parainfluenza haemagglutinin-neuraminidase functions. This may be considered in terms of blocking the haemagglutination function and/or the neuraminidase (enzyme) function. While antiviral compounds have been disclosed in the present Applicant's earlier filed International Application, published as WO 2016/033660, as modulators of the viral haemagglutinin-neuraminidase the present application provides new compound templates which were not envisaged in that earlier publication which have led to a more complete exploitation of the hPIV HN binding pocket.

In particular, the inventors have performed extensive structural biology and computational studies of human parainfluenza virus (hPIV) haemagglutinin-neuraminidase (HN), and have identified amino acid residues surrounding the substrate binding site that engage the $R_3$ substituent of Formula (I), and spatial requirements for the $R_3$ substituent, which enhance the binding affinity of inhibitors based on Formula (I), and Formulae (II) and (BI). X-ray crystallographic studies [including co-crystal structures of hPIV-3 HN in complex with IE 1993-40, $JC_{2001}$-48 and RP1967-89] identified amino acids surrounding the substrate binding site that engage with the $R_3$ substituent, as mainly polar and/or charged, which display strong hydrogen bond donors and/or acceptors. This suggests favourable binding interactions for $R_3$ substituents that incorporate a heterocyclic ring, especially the substituents detailed in paragraphs [0020]-[0043] below.

In some embodiments of compounds of Formula (I), Formula (II) or Formula (BI), one or more of the features of paragraphs to may apply (the features of paragraphs [0015] to [0052] may apply alone or in combination with features of any others of paragraphs [0015] to [0052]). For the avoidance of doubt, any of the definitions of $R_1$, $R_3$, $R_4$, $R_6$, $R_7$ and $R_8$ may be combined with any other definitions of $R_1$, $R_3$, $R_4$, $R_6$, $R_7$ and $R_8$ described herein.

In one embodiment of the compound of Formula (I), (II) or (III), $R_1$ is selected from the group consisting of COOH, or a salt thereof, $C(O)NR_9R_{10}$, and $C(O)OR_{11}$ wherein $R_9$, $R_{10}$ and $R_{11}$ are independently selected from the group consisting of hydrogen, $C_1$-$C_6$ alkyl, aryl, heteroaryl and heterocyclyl; wherein said $C_1$-$C_6$ alkyl, aryl, heteroaryl and heterocyclyl are optionally substituted (especially by one or more $R_{50}$). In another embodiment, $R_1$ is selected from the group consisting of COOH, or a salt thereof, and $C(O)OR_{11}$ wherein $R_{11}$ is independently selected from the group consisting of hydrogen, $C_1$-$C_6$ alkyl, aryl, heteroaryl and heterocyclyl; wherein said $C_1$-$C_6$ alkyl, aryl, heteroaryl and heterocyclyl are optionally substituted (especially by one or more $R_{50}$).

In one embodiment, $R_{50}$ is selected from the group consisting of: $R_{53}$, —O—$R_{53}$, —C(O)—$R_{53}$, —C(O)—O—$R_{53}$, —O—C(O)—$R_{53}$, CN, OH, oxo, $NR_{51}R_{51}'$, Cl, F, Br, I, aryl optionally substituted by at least one $R_{52}$ and heterocyclyl optionally substituted by at least one $R_{52}$; wherein $R_{51}$ and $R_{51}'$ are independently selected from hydrogen, $C_1$-$C_9$ alkyl, $C_1$-$C_9$ haloalkyl, C═O—$C_1$-$C_9$ alkyl, $SO_2$—$C_1$-$C_9$ alkyl and C═O—NH—$C_1$-$C_9$ alkyl; wherein $R_{52}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{51}R_{51}'$, Cl, F, Br and I; wherein $R_{53}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl. In one embodiment, $R_{50}$ is selected from the group consisting of: $R_{53}$, —O—$R_{53}$, —C(O)—$R_{53}$, —C(O)—O—$R_{53}$, —O—C(O)—$R_{53}$, CN, OH, oxo, Cl, F, Br and I; wherein $R_{53}$ is selected from the group consisting of: $C_1$-$C_6$ alkyl and $C_1$-$C_6$ haloalkyl. In one embodiment, $R_{50}$ is selected from the group consisting of: $R_{53}$, Cl, F and Br; wherein $R_{53}$ is selected from the group consisting of: $C_1$-$C_6$ alkyl and $C_1$-$C_6$ haloalkyl.

In one embodiment of the compound of Formula (I), (II) or (II), $R_1$ is COOH, or a salt thereof, or $C(O)OR_{11}$ wherein $R_{11}$ is selected from methyl, ethyl and propyl.

In certain specific embodiments $R_1$ is selected from the group consisting of COOH, COONa and C(O)OMe.

In one embodiment of the compounds of Formula (I), (II) or (III), ring W, together with the carbon atoms to which it is attached, form a monocyclic heterocyclic ring which may be optionally substituted (especially by one or more $R_{55}$) or a fused bicyclic heterocyclic ring which may be optionally substituted (especially by one or more $R_{55}$). In another embodiment of the compounds of Formula (I), (II) or (III), ring W, together with the carbon atoms to which it is attached, form a monocyclic heteroaryl ring which may be optionally substituted (especially by one or more $R_{55}$) or a fused bicyclic heteroaryl ring which may be optionally substituted (especially by one or more $R_{55}$).

In one embodiment of the compounds of Formula (I), (II) or (III), $R_3$ is selected from the group consisting of: thienopyrrolyl, pyridinopyrrolyl, pyrazinopyrrolyl, thiazolopyrrolyl, dioxoloisoindolyl, indolopyrrolyl, benzofuropyrrolyl, thienopyrrolyl, imidazoisoindolyl, thienoisoindolyl and furoisoindolyl; wherein any of the aforementioned groups may be optionally substituted (especially by one or more $R_{55}$). In one embodiment of the compounds of Formula (I), (II) or (III), $R_3$ is thienopyrrolyl which may be optionally substituted (especially by one or more $R_{55}$).

In one embodiment of the compounds of Formula (I), (II) or (III), $R_3$ is selected from the group consisting of: 5H-thieno[2,3-c]pyrrolyl, 6H-pyrrolo[3,4-b]pyridine, 2H-pyrrolo[3,4-c]pyridine, 6H-pyrrolo[3,4-b]pyrazine, 5H-pyrrolo[3,4-d]thiazole, 7H-[1,3]dioxolo[4,5-e]isoindolyl, 2,4-dihydropyrrolo [3,4-h]indole, 2H-benzofuro[2,3-c] pyrrolyl, 2H-benzo[4,5]thieno[2,3-c]pyrrolyl, 1,7-dihydroimidazo [4,5-e]isoindolyl, 7H-thieno [2,3-e]isoindolyl, 6H-thieno[2,3f]isoindolyl, and 6H-furo[2,3-f]isoindolyl; wherein any of the aforementioned groups may be optionally substituted (especially by one or more $R_{55}$).

In one embodiment of the compounds of Formula (I), (II) or (III), $R_3$ is selected from the group consisting of:
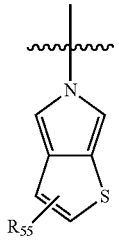
,
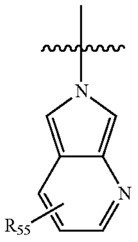
,
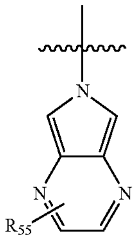
,
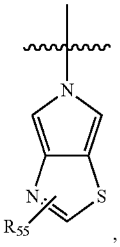
,
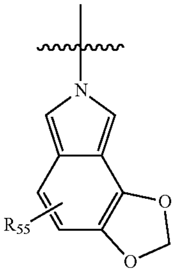
,
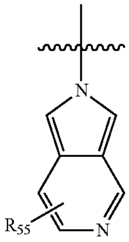
,
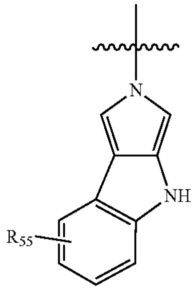
,
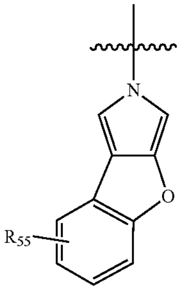
,
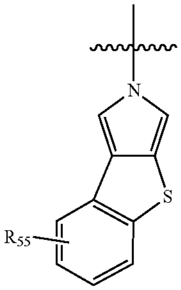
,
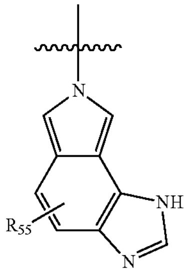
,
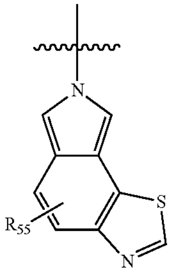
,
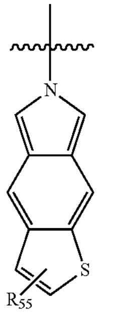
, and
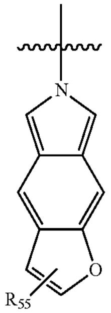
.
In one embodiment, $R_3$ is
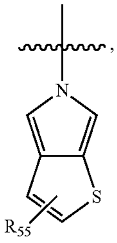
,
In one embodiment of the compounds of Formula (I), (II) or (III), $R_3$ is selected from the group consisting of:
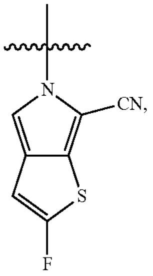
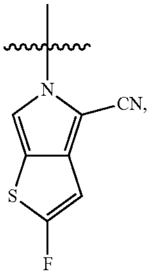
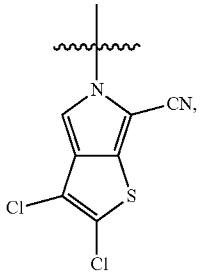
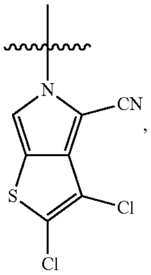
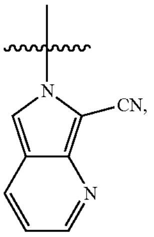
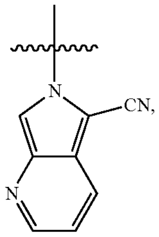
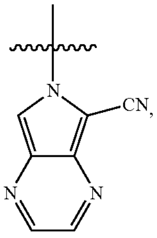
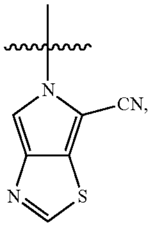
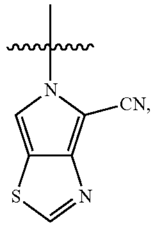
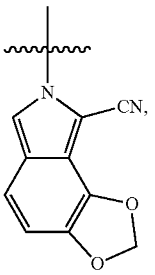
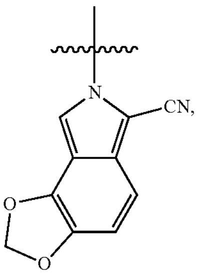
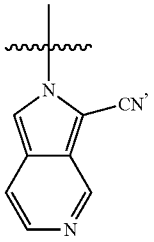

-continued

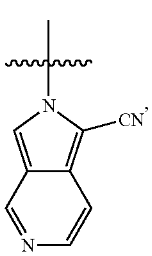 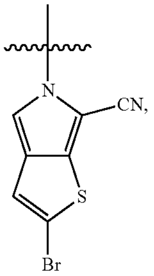 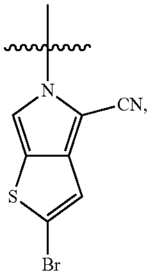

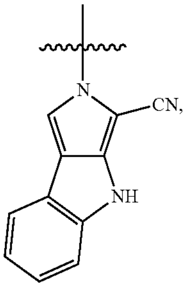 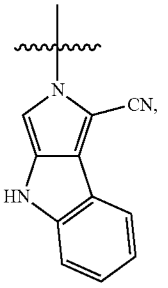 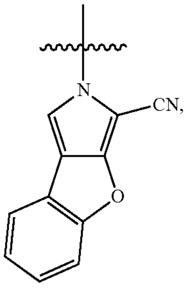

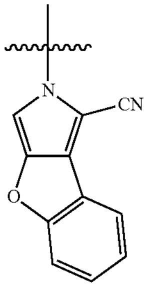 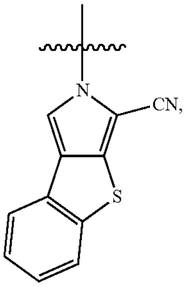 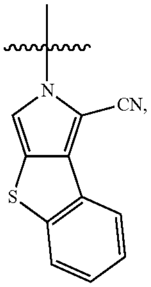

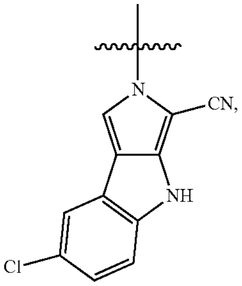 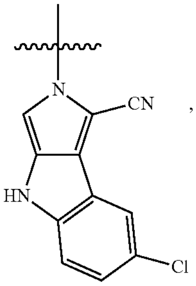

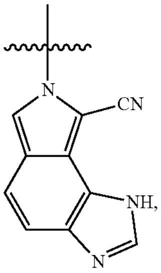 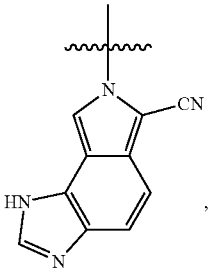

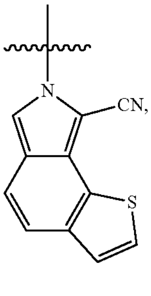 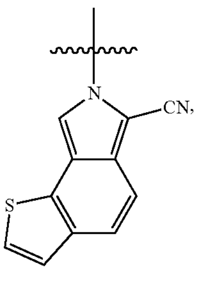 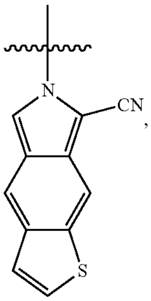

-continued

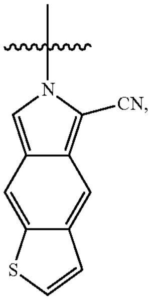 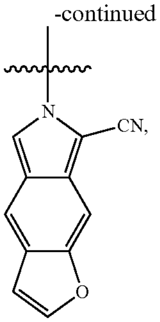 and 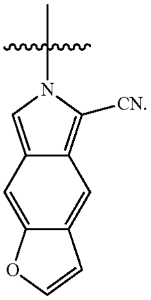

In one embodiment, $R_3$ is

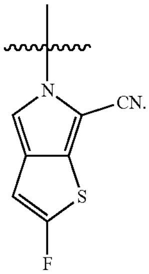 [SMILES: *n1cc2cc(F)sc2c1C#N]

In one embodiment, $R_{55}$ is selected from the group consisting of: $C_1$-$C_6$ alkyl, $C_1$-$C_6$ haloalkyl, $C_1$-$C_6$ alkoxy, $C_1$-$C_6$ haloalkoxy, CN, OH, oxo, $NR_{56}R_{56}'$, Cl, F and Br; wherein $R_{56}$ and $R_{56}'$ are independently selected from hydrogen, $C_1$-$C_9$ alkyl, $C_1$-$C_9$ haloalkyl, C═O—$C_1$-$C_9$ alkyl, $SO_2$—$C_1$-$C_9$ alkyl and C═O—NH—$C_1$-$C_9$ alkyl. In another embodiment, $R_{55}$ is selected from the group consisting of: $C_1$-$C_6$ alkyl, $C_1$-$C_6$ haloalkyl, $C_1$-$C_6$ alkoxy, $C_1$-$C_6$ haloalkoxy, CN, OH, oxo, Cl, F and Br. In a further embodiment, $R_{55}$ is selected from the group consisting of CN, F, Cl and Br. In one embodiment, the compound comprises at least one $R_{55}$, wherein said $R_{55}$ is CN; especially wherein said CN is geminal to the ring nitrogen of the pyrrole moiety of $R_3$.

In one embodiment of the compounds of Formula (I), (II) or (III), ring Y, together with the carbon atoms to which it is attached, form a monocyclic heterocyclic ring which may be optionally substituted (especially by one or more $R_{60}$) or a monocyclic heteroaryl ring which may be optionally substituted (especially by one or more $R_{60}$); and ring Z, together with two ring atoms of ring Y, form a monocyclic heterocyclic ring which may be optionally substituted (especially by one or more $R_{60}$), a monocyclic heteroaryl ring which may be optionally substituted (especially by one or more $R_{60}$), a monocyclic cycloalkyl ring which may be optionally substituted (especially by one or more $R_{60}$), a monocyclic cycloalkenyl ring which may be optionally substituted (especially by one or more $R_{60}$), or a monocyclic aryl ring which may be optionally substituted (especially by one or more $R_{60}$), or may be absent.

In one embodiment of the compounds of Formula (I), (II) or (III), $R_3$ is selected from the group consisting of: pyridinopyrazolyl, thienopyrazolyl, furopyrazolyl, pyrrolopyrazolyl, imidazopyrazolyl, isoxazolopyrazolyl, pyridinoimidazopyrazolyl, benzothienopyrazolyl and indolopyrazolyl; wherein any of the aforementioned groups may be optionally substituted (especially by one or more $R_{60}$). In one embodiment, $R_3$ is pyridinopyrazolyl, which may be optionally substituted (especially by one or more $R_{60}$).

In one embodiment of the compounds of Formula (I), (II) or (III), $R_3$ is selected from the group consisting of: 2H-pyrazolo[3,4-c]pyridine, 2H-pyrazolo[3,4-b]pyridine, 2H-pyrazolo[4,3-c]pyridine, 2H-pyrazolo[4,3 -b]pyridine, 2H-thieno[3,2-c]pyrazolyl, 2H-thieno[2,3-c]pyrazolyl, 2H-furo[2,3-c]pyrazolyl, 2H-furo[3,2-c]pyrazolyl, 2,4-dihydropyrrolo[3,2-c]pyrazolyl, 2,6-dihydropyrrolo[2,3-c]pyrazolyl, 2,6-dihydroimidazo[4,5-c]pyrazolyl, 5H-pyrazolo [3,4-d]isoxazole, 2H-pyrazolo[4',3':4,5]imidazo [1,2-a]pyridine, 2H-benzo [4,5]thieno[2,3-c]pyrazolyl, and 2,8-dihydropyrazolo[3,4-b]indole; wherein any of the aforementioned groups may be optionally substituted (especially by one or more $R_{60}$).

In one embodiment of the compounds of Formula (I), (II) or (III), $R_3$ is selected from the group consisting of:

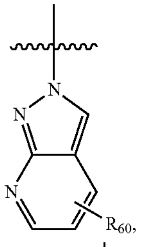
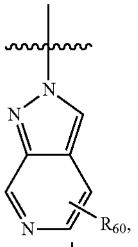
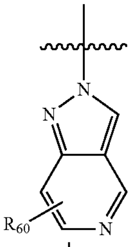
,
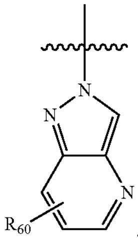
,
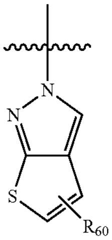
,
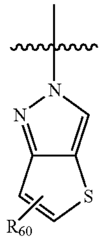
,
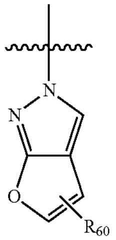
,
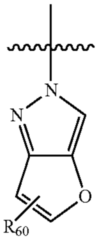
,
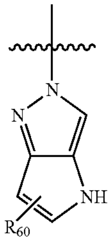
,
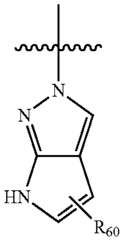
,
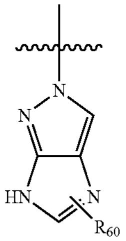
,
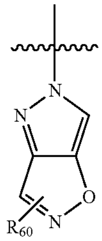
,
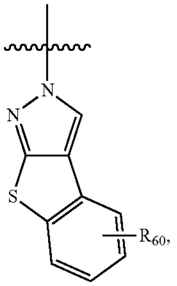
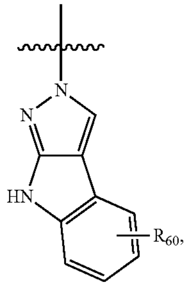
and -continued

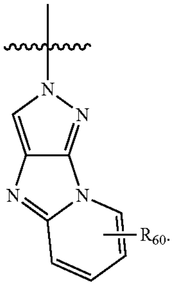

In one embodiment of the compounds of Formula (I), (II) or (III), $R_3$ is selected from the group consisting of:

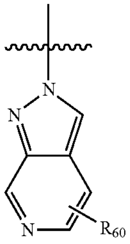
and
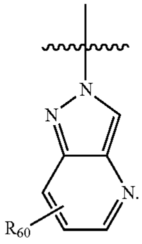

In one embodiment of the compounds of Formula (I), (II) or (III), $R_3$ is selected from the group consisting of:

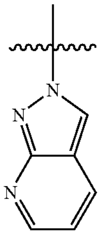
,
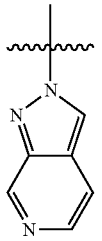
,
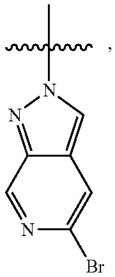
,
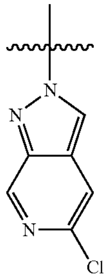
,
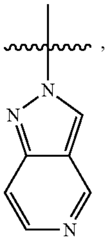
,
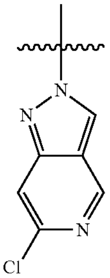
,
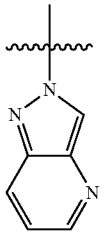
,
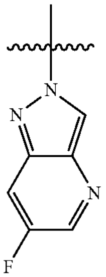
,
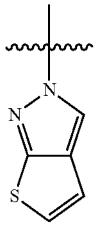
, -continued

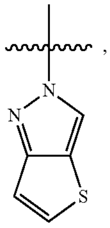,
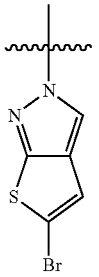,
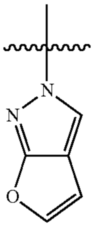,
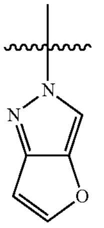,
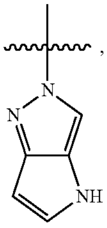,
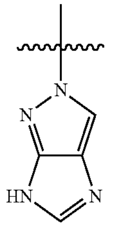,
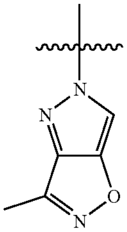,
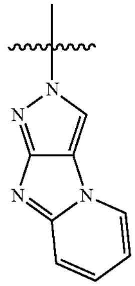,
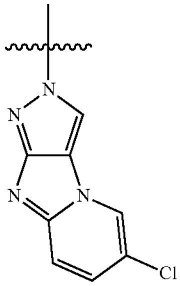,
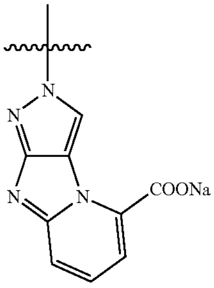,
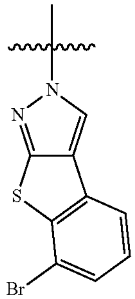,
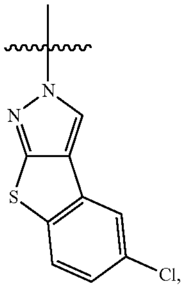
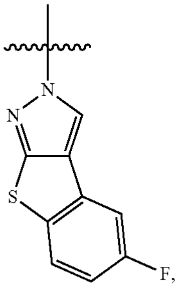
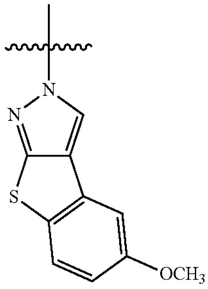
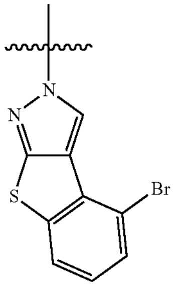
and -continued

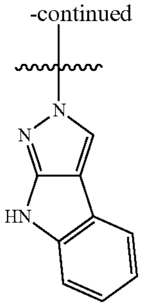.

In one embodiment of the compounds of Formula (I), (II) or (III), $R_3$ is selected from the group consisting of

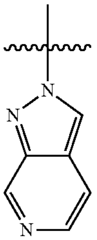
and
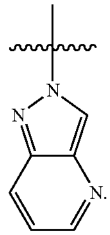

In one embodiment, $R_{60}$ is selected from the group consisting of: $R_{63}$, —O—$R_{63}$, —S—$R_{63}$, C(O)—$R_{63}$, —C(S)—$R_{63}$, —C(O)—O—$R_{63}$, —C(O)—OH (or a salt thereof), —O—C(O)—$R_{63}$, —O—C(S)—$R_{63}$, -C(S)—O—$R_{63}$, CN, OH, oxo, $NR_{61}R_{61}'$, Cl, F, and Br; wherein $R_{61}$ and $R_{61}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C=O-$C_1$-$C_9$ alkyl, $SO_2$-$C_1$-$C_9$ alkyl and C═O—NH—$C_1$-$C_9$ alkyl; wherein $R_{63}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl. In one embodiment, $R_{60}$ is selected from the group consisting of: $R_{63}$, —O—$R_{63}$, —C(O)—O≤$R_{63}$, —C(O)—OH (or a salt thereof), Cl, F, and Br; wherein $R_{63}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl (especially $C_1$-$C_6$ alkyl or $C_1$-$C_6$ haloalkyl). In one embodiment, $R_{60}$ is selected from the group consisting of Br, F, Cl, —$OCH_3$, COOH or a salt thereof, and $CH_3$.

In one embodiment of the compounds of Formula (I), (II) or (III), ring Y, together with the carbon atoms to which it is attached, form a phenyl ring which may be optionally substituted (especially by one or more $R_{65}$); and ring Z, together with two ring atoms of ring Y, form a monocyclic heterocyclic ring which may be optionally substituted (especially by one or more $R_{65}$), or a monocyclic heteroaryl ring which may be optionally substituted (especially by one or more $R_{65}$), wherein said monocyclic heterocyclic or heteroaryl ring comprises at least one N ring atom.

In one embodiment of the compounds of Formula (I), (II) or (III), $R_3$ is

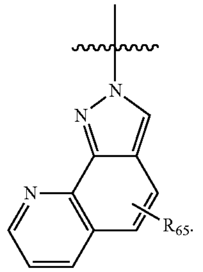

In another embodiment, $R_3$ is

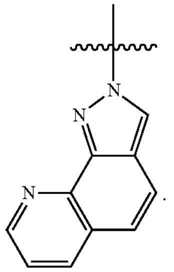 [SMILES: *n1cc2ccc3cccnc3c2n1]

In one embodiment, $R_3$ is not

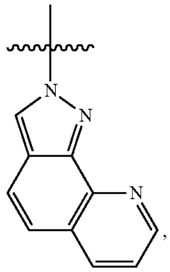,
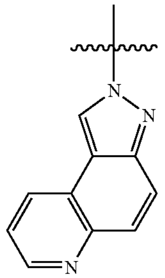, or
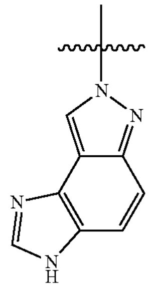.

In one embodiment, ring Z does not form a 1,3-dioxolane. In one embodiment, when ring Z forms a pyridyl, the pyridyl nitrogen does not form a bond to a carbon atom of ring Y.

In one embodiment, $R_{65}$ may be selected from the group consisting of: $R_{68}$, —O—$R_{68}$, —S—$R_{68}$, —C(O)-$R_{68}$, —C(S)—$R_{68}$, —C(O)—O—$R_{68}$, —O—C(O)—$R_{68}$, —C(S)—$R_{68}$, —C(S)—O—$R_{68}$, CN, OH, oxo, $NR_{66}R_{66}'$, Cl, F, Br; wherein $R_{66}$ and $R_{66}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$—$C_1$-$C_9$ alkyl and C═O—NH—$C_1$-$C_9$ alkyl; wherein $R_{68}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl. In one embodiment, $R_{65}$ may be selected from the group consisting of: $R_{68}$, —O—$R_{68}$, —C(O)—$R_{68}$, —C(O)—O—$R_{68}$, —O—C(O)—$R_{68}$, CN, OH, oxo, $NR_{66}R_{66}'$, Cl, F, Br; wherein $R_{66}$ and $R_{66}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$-$C_1$-$C_9$ alkyl and C═O—NH—$C_1$-$C_9$ alkyl; wherein $R_{68}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl. In one embodiment, $R_{65}$ may be selected from the group consisting of: $R_{68}$, —O—$R_{68}$, —C(O)—$R_{68}$, —C(O)—O—$R_{68}$, —O—C(O)—$R_{68}$, CN, OH, oxo, Cl, F, Br; wherein $R_{68}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl (especially $C_1$-$C_6$ alkyl or $C_1$-$C_6$ haloalkyl).

In one embodiment of the compounds of Formula (I), (II) or (III), ring X, together with the carbon atoms to which it is attached, form a monocyclic heterocyclic ring which may be optionally substituted (especially by one or more $R_{70}$), a monocyclic heteroaryl ring which may be optionally substituted (especially by one or more $R_{70}$), a fused bicyclic heterocyclic ring which may be optionally substituted (especially by one or more $R_{70}$), or a fused bicyclic heteroaryl ring which may be optionally substituted (especially by one or more $R_{70}$). In one embodiment, ring X, together with the carbon atoms to which it is attached, form a monocyclic heteroaryl ring which may be optionally substituted (especially by one or more $R_{70}$), or a fused bicyclic heteroaryl ring which may be optionally substituted (especially by one or more $R_{70}$).

In one embodiment of the compounds of Formula (I), (II) or (III), $R_3$ is selected from the group consisting of: pyridinotriazolyl, indolotriazolyl and dioxolobenzotriazolyl, wherein any of the aforementioned groups may be optionally substituted (especially by one or more $R_{70}$). In one embodiment, $R_3$ is indolotriazolyl which may be optionally substituted (especially by one or more $R_{70}$).

In one embodiment of the compounds of Formula (I), (II) or (III), $R_3$ is selected from the group consisting of: 1H-[1,2,3]triazolo[4,5-c]pyridine, 3H-[1,2,3]triazolo[4,5-c]pyridine, 3,6-dihydro-[1,2,3]triazolo[4,5-e]indole, 1,6-dihydro-[1,2,3]triazolo[4,5-e]indole, and 1H-[1,3]dioxolo[4',5':4,5]benzo[1,2-d][1,2,3] triazole, wherein any of the aforementioned groups may be optionally substituted (especially by one or more $R_{70}$).

In one embodiment of the compounds of Formula (I), (II) or (III), $R_3$ is selected from the group consisting of:

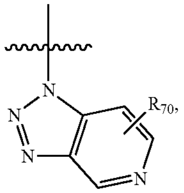,
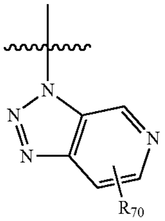,

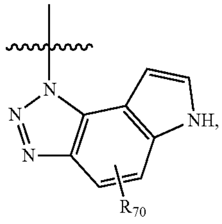,
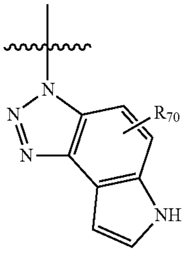, and

-continued

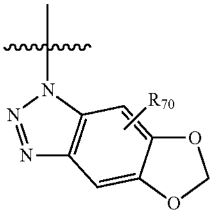

;

especially

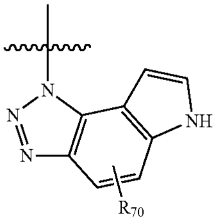

or

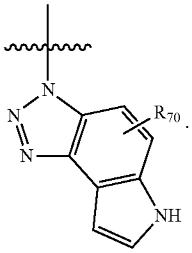

.

In one embodiment of the compounds of Formula (I), (II) or (III), $R_3$ is selected from the group consisting of:

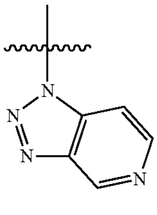

,

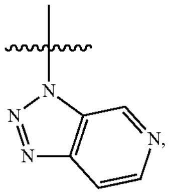

,

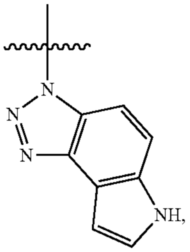

,

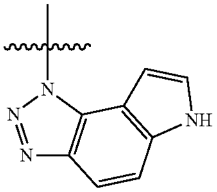

,

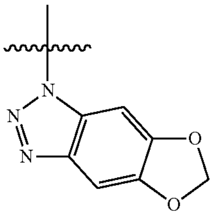

;

especially

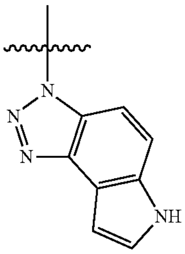

or

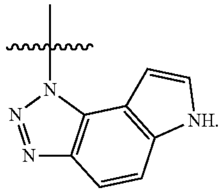

.

In one embodiment of the compounds of Formula (I), (II) or (III), ring X, together with the carbon atoms to which it is attached, form a phenyl ring substituted by a heterocyclic or heteroaryl ring, wherein said phenyl, heterocyclic and/or heteroaryl ring are optionally substituted (especially by one or more $R_{70}$). In one embodiment, said heterocyclic ring is a morpholino group.

In one embodiment of the compounds of Formula (I), (II) or (III), $R_3$ is

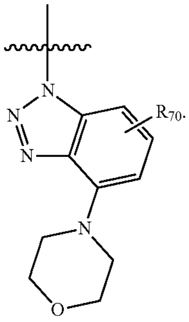

.

In one embodiment, $R_3$ is

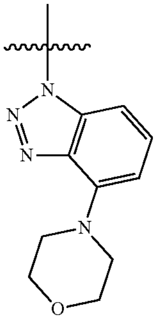 [SMILES: *n1nnc2c(N3CCOCC3)cccc21]

In one embodiment, $R_{70}$ is selected from the group consisting of: $R_{73}$, —O—$R_{73}$, —S—$R_{73}$, —C(O)—$R_{73}$, —C(S)—$R_{73}$, —C(O)—O—$R_{73}$, —O—C(O)—$R_{73}$, —O—C(S)—$R_{73}$, —C(S)—O—-$R_{73}$, CN, OH, oxo, $NR_{71}R_{71}'$, Cl, F and Br; wherein $R_{71}$ and $R_{71}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$-$C_1$-$C_9$ alkyl and C═O—NH—$C_1$-$C_9$ alkyl; wherein $R_{73}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$ -$C_6$ alkynyl, and $C_2$-$C_6$ haloalkynyl.

In one embodiment, $R_{70}$ is selected from the group consisting of: $R_{73}$, —O—$R_{73}$, —C(O)—$R_{73}$, —C(O)—O-$R_{73}$, —O—C(O)—$R_{73}$, CN, OH, oxo, $NR_{71}R_{71}'$, Cl, F and Br; wherein $R_{71}$ and $R_{71}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$-$C_1$-$C_9$ alkyl and C═O—NH—$C_1$-$C_9$ alkyl; wherein $R_{73}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl. In one embodiment, $R_{70}$ is selected from the group consisting of: $R_{73}$, —O—$R_{73}$, —C(O)—$R_{73}$, —C(O)—O—$R_{73}$, —O—C(O)—$R_{73}$, CN, OH, oxo, Cl, F and Br; wherein $R_{73}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl. $R_{73}$ may be $C_1$-$C_6$ alkyl or $C_1$-$C_6$ haloalkyl.

In one embodiment of the compounds of Formula (I), (II) or (III), $R_3$ is selected from the group consisting of:

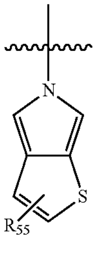 , 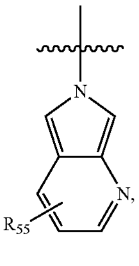 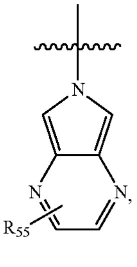 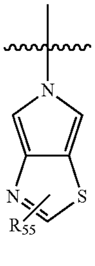 ,

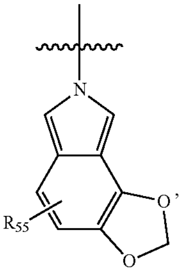 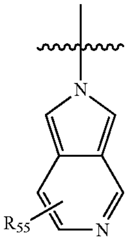 , 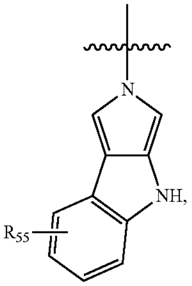

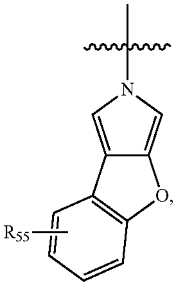 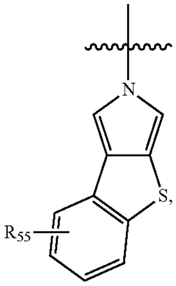 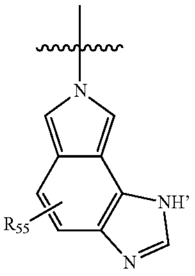

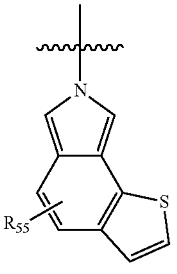 , 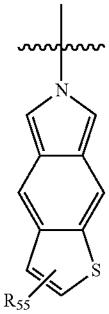 , 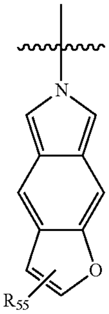 ,

-continued

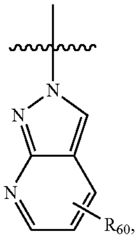 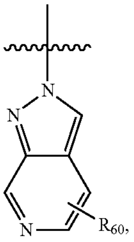 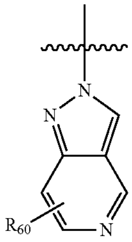 ,

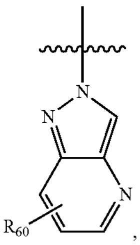 , 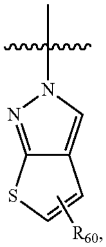 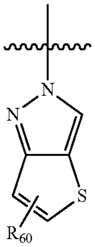 , 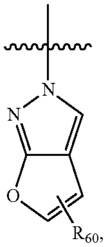

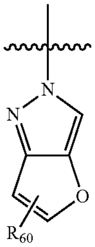 , 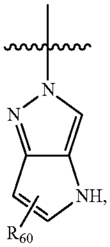 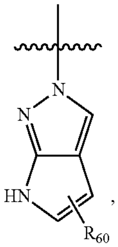 , 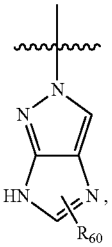

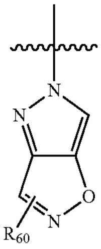 , 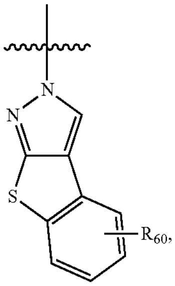 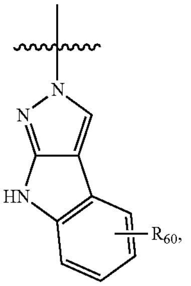

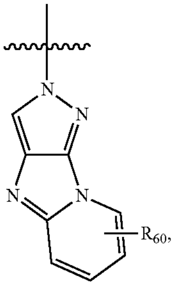 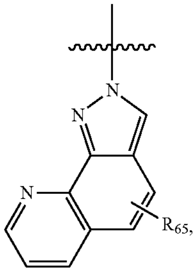

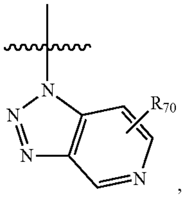 , 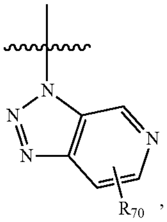 ,

-continued
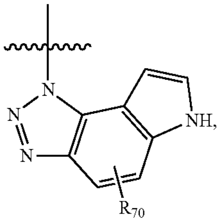
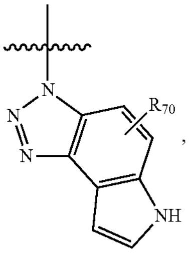
, and
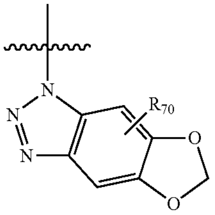
.
In one embodiment of the compounds of Formula (I), (II) or (III), $R_3$ is selected from the group consisting of:
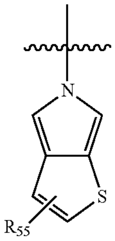
,
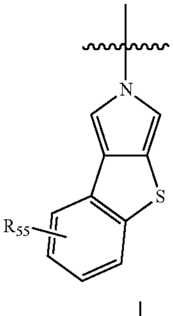
,
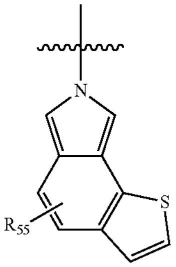
,
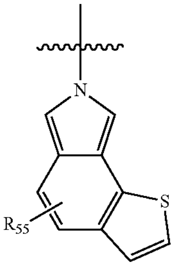
,
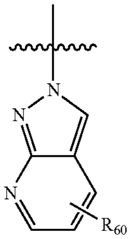
,
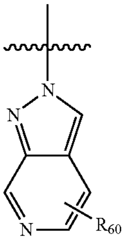
,
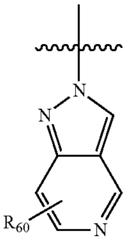
,
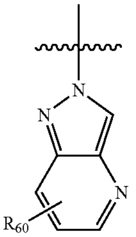
,
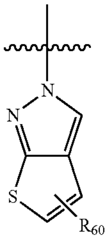
,
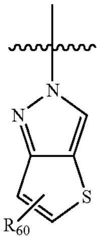
,
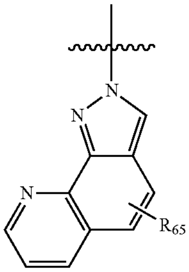
,
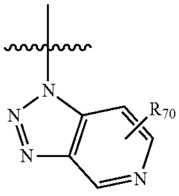
,
-continued
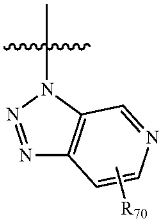
,
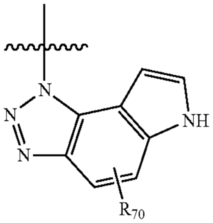
, and
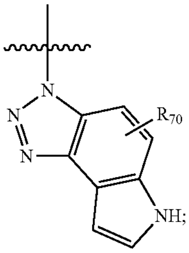
especially
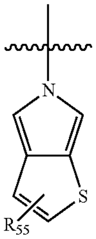
,
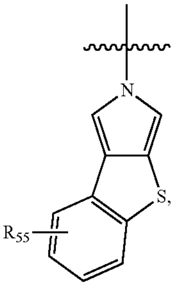
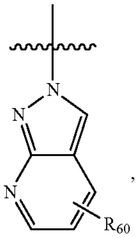
,
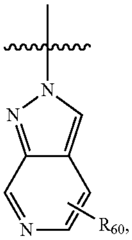
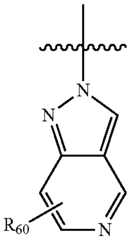
,
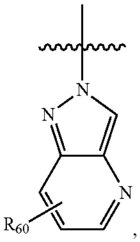
,
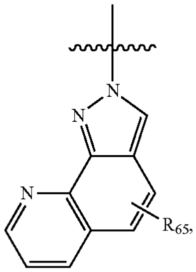
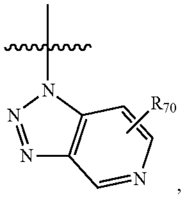
,
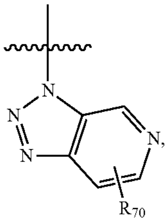
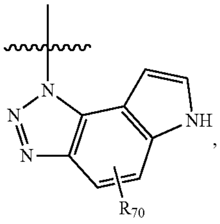
, and -continued

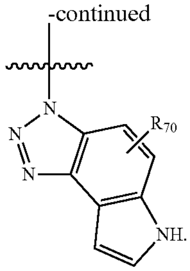

In the above, groups $R_{55}$, $R_{60}$, $R_{65}$, $R_{70}$ may be as defined above. In one embodiment of the compounds of Formula (I), (II) or (III), $R_3$ is selected from the group consisting of: the substituents listed in paragraph [0023], the substituents listed in paragraph [0029],

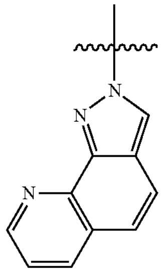, the substituents listed in paragraph [0039], and

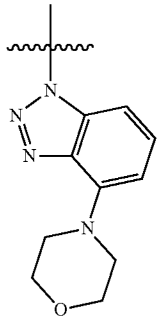.

The specific moieties or the disclosure of any $R_3$ group listed above may be combined with any disclosure of an $R_1$, $R_4$, $R_6$, $R_7$ or $R_8$ group as described herein.

$R_4$ may be selected from the group consisting of NH—C(O)$R_{17}$, —NHS(O)$_2R_{27}$ wherein $R_{27}$ is selected from the group consisting of $C_1$-$C_6$ alkyl, $C_1$-$C_6$ haloalkyl and $C_3$-$C_6$ cycloalkyl, all of which may be optionally substituted (especially by one of more $R_{75}$ as previously defined), and —NHC(O)NH$R_{17}$ wherein $R_{17}$ may be as previously defined. In one embodiment of any of the formulae described for the first aspect, $R_4$ is NHC(O)$R_{17}$ wherein $R_{17}$ is selected from the group consisting of $C_1$-$C_6$ alkyl, $C_1$-$C_6$ haloalkyl and $C_3$-$C_6$ cycloalkyl; wherein said $C_1$-$C_6$ alkyl, $C_1$-$C_6$ haloalkyl and $C_3$-$C_6$ cycloalkyl may be optionally substituted (especially by one or more $R_{75}$). In one embodiment of any of the formulae described for the first aspect, $R_4$ is NHC(O)$R_{17}$ wherein $R_{17}$ is selected from the group consisting of $C_1$-$C_6$ alkyl and $C_1$-$C_6$ haloalkyl; especially $R_{17}$ is —CH—$(CH_3)_2$ or —$CF_3$. In one embodiment of any of the formulae described for the first aspect, $R_4$ is selected from the group consisting of:

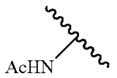, 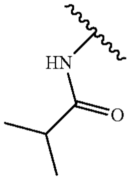, 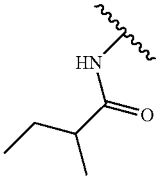,

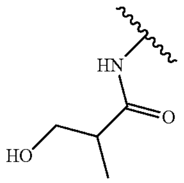, 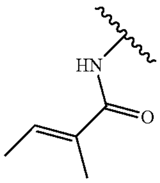, 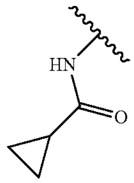,

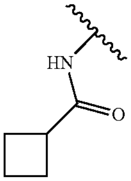, 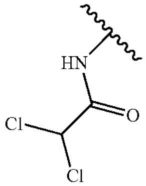, 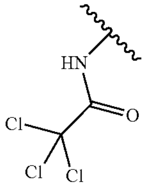,

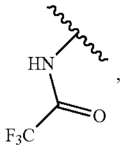, 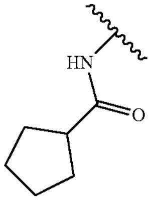, 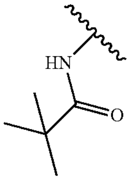,

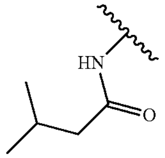, 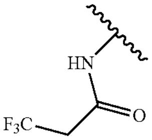, 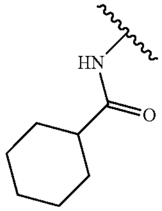,

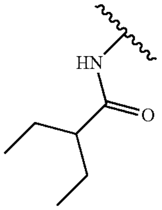, 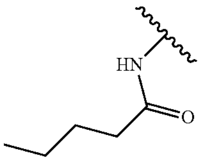, 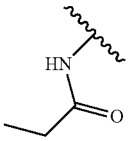,

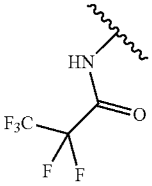, 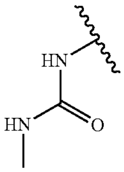, 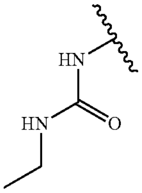,

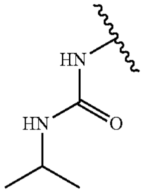, 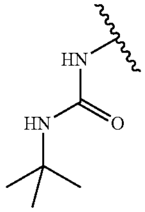, 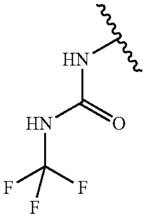,

-continued

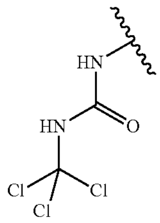 , 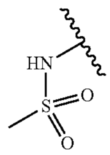 , 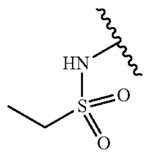 ,

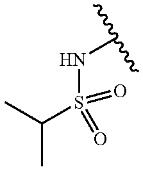 , 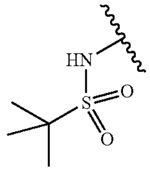 , 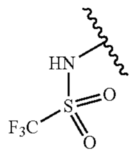 ,

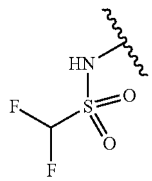 , 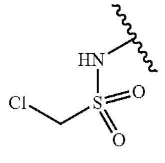 , 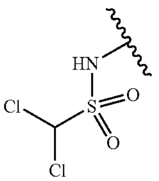 and

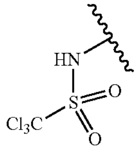 .

In embodiments of any of the formulae described for the first aspect, $R_4$ is selected from the group consisting of —NHAc, —NHC(O)CH$(CH_3)_2$, —NHC(O)$CF_3$ and —NHC(O)$CH_2CH_3$.

In one embodiment, $R_{75}$ is selected from the group consisting of: $R_{78}$, —O—$R_{78}$, —S—$R_{78}$, —C(O)—$R_{78}$, —C(S)—$R_{78}$, —C(O)—O—$R_{78}$, —O—C(O)—$R_{78}$, —O—C(S)—$R_{78}$, —C(S)—O—$R_{78}$, CN, OH, oxo, $NR_{76}R_{76}$', Cl, F, and Br; wherein $R_{76}$ and $R_{76}$' are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$—$C_1$-$C_9$ alkyl and C═O—NH—$C_1$-$C_9$ alkyl; wherein $R_{78}$ is selected from the group consisting of: $C_1$-$C_6$ alkyl, $C_1$-$C_6$ haloalkyl, $C_2$-$C_6$ alkenyl, $C_2$ -$C_6$ haloalkenyl, $C_2$-$C_6$ alkynyl, and $C_2$-$C_6$ haloalkynyl. In one embodiment, $R_{75}$ is selected from the group consisting of: $R_{78}$, —O—$R_{78}$, CN, OH, oxo, Cl, F, and Br; wherein $R_{78}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl (especially wherein $R_{78}$ is $C_1$-$C_6$ alkyl or $C_1$-$C_6$ haloalkyl).

In any embodiment of the compounds of Formula (I), (II) or (III), $R_6$, $R_7$ and Ra may be independently selected from the group consisting of OH, $C_1$-$C_3$ alkoxy, —OC(O)$R_{18}$ wherein $R_{18}$ is optionally substituted $C_1$-$C_3$ alkyl (especially by one or more $R_{80}$ as previously defined), and —$NR_{18}R_{18}$' wherein $R_{18}$ and $R_{18}$' are selected from hydrogen, optionally substituted $C_1$-$C_3$ alkyl (especially by one or more $R_{80}$ as previously defined) and optionally substituted $C_1$-$C_6$ alkanoyl (especially by one or more $R_{80}$ as previously defined). When $R_{18}$ is C(O)R (i.e. alkanoyl) then 'R' may be $C_1$-$C_6$ alkyl or $C_5$-$C_6$ cycloalkyl.

In embodiments of any of the formulae described for the first aspect, $R_6$, $R_7$ and $R_8$ may be independently selected from OH and OAc.

In embodiments of any of the formulae described for the first aspect, $R_6$, $R_7$ and $R_8$ may be independently selected from the group consisting of OH, $R_{19}$, —$R_{19}$, $NR_{18}R_{18}$', —OC(O)$R_{18}$, —NH(C═O)$R_{18}$, and $S(O)_{nR}R_{18}$, wherein n=0-2 and each Rig and $R_{18}$' are independently selected from hydrogen, optionally substituted $R_{19}$ (especially by one or more $R_{80}$) and optionally substituted $C_1$-$C_9$ alkanoyl (especially by one or more $R_{80}$); wherein each $R_{19}$ is independently selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl (especially $C_1$-$C_6$ alkyl or $C_1$-$C_6$ haloalkyl).

In one embodiment, $R_{80}$ is selected from the group consisting of: $R_{83}$, —O—$R_{83}$, —C(O)—$R_{83}$, —C(S)—$R_{83}$, —C(O)—O—$R_{83}$, —O—C(O)—$R_{83}$, CN, OH, oxo, $NR_{81}R_{81}$', Cl, F and Br; wherein $R_{81}$ and $R_{81}$' are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$—-$C_1$-$C_9$ alkyl and C═O—NH—$C_1$-$C_9$ alkyl; wherein $_{83}$ is selected from the group consisting of: $C_1$-$C_6$ alkyl, $C_1$-$C_6$ haloalkyl, $C_2$ -$C_6$ alkenyl, $C_2$-$C_6$ haloalkenyl, $C_2$-$C_6$ alkynyl, and $C_2$-$C_6$ haloalkynyl. In one embodiment, $R_{80}$ is selected from the group consisting of: $R_{83}$, —O—$R_{83}$, —C(O)—$R_{83}$, —C(S)—$R_{83}$, —C(O)—O—$R_{83}$, —O—C(O)—$R_{83}$, CN, OH, oxo, Cl, F and Br; wherein $R_{83}$ is selected from the group consisting of: $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl. In one embodiment, $R_{83}$ is $C_1$-$C_6$ alkyl or $C_1$-$C_6$ haloalkyl.

In one embodiment, the compound of Formula (I), (II) or (III) is not

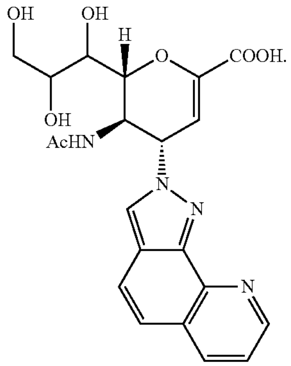 [SMILES: CC(=O)N[C@H]1[C@H](C(O)C(O)CO)OC(C(=O)O)=C[C@@H]1n1cc2ccc3cccnc3c2n1]

In one embodiment, the compound of Formula (I), (II) or (III) is not

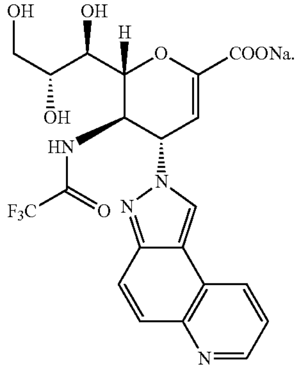

In one embodiment, the compound of Formula (I), (II) or (III) is not
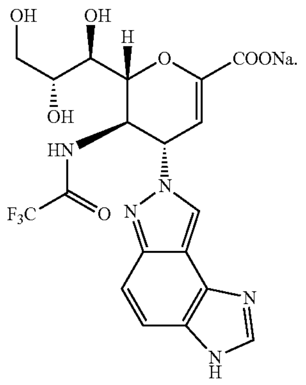
In one embodiment, the compound of Formula (I), (II) or (III) is not
RP1967-89
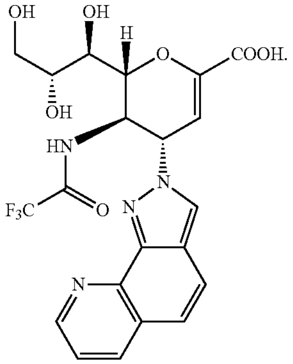
In embodiments of formula (I) and formula (II) the compound may be selected from the group consisting of:
IE1993-40
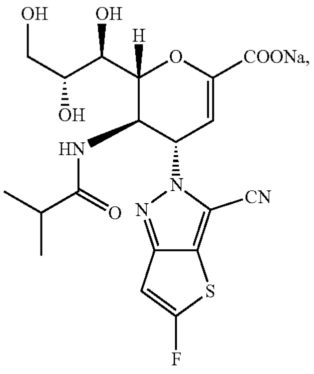
-continued
JC2001-48
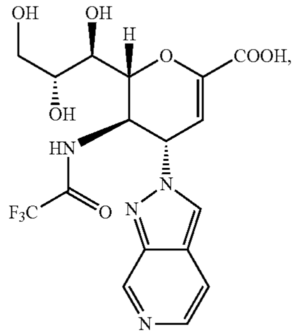
JC2001-49
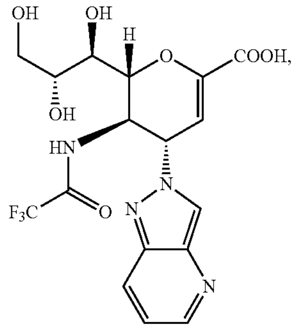
RP1967-89
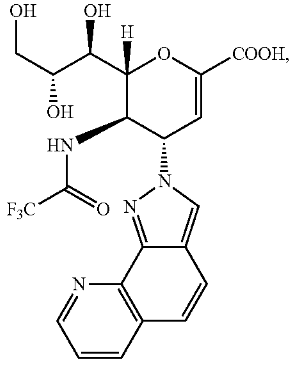
IE1963-113a
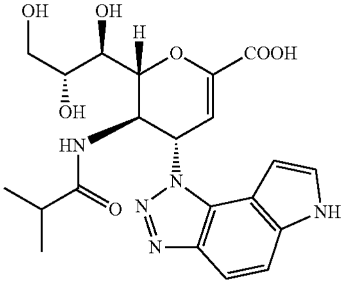
and -continued IE1963-113b

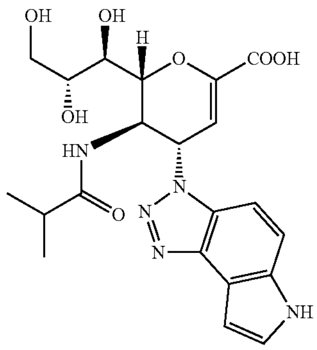

and protected forms thereof, including acetyl replacing hydrogen at the free hydroxyls, all C-2 analogues thereof wherein the C-2 carboxy group is in the protonated form, sodium salt form or prodrug form and wherein each compound may be considered to have close analogues disclosed wherein the $R_4$ position is explicitly replaced with any —NHC(O)R group wherein R is $C_1$-$C_4$ alkyl or haloalkyl.

It will be appreciated by a person of skill in the art of synthetic chemistry that the COOH group is easily interchanged with a salt form or an ester protecting group, for example a methyl ester group, and so all such forms are considered to be disclosed herein with reference to the compounds listed above.

The prodrug form of the above compounds may be explicitly considered to include $C_1$-$C_{20}$ ester or ester comprising a cycloalkyl, or aryl moiety. The aryl moiety may include substituted phenyl or fused 2-3 cyclic aromatic rings.

In one embodiment, the compound of the first aspect is a haemagglutinin-neuraminidase modulator. That is, the compound of the first aspect is a modulator of haemagglutinin and/or neuraminidase functions. Preferably, the compound of the first aspect is a haemagglutinin-neuraminidase inhibitor. That is, an inhibitor of haemagglutinin and/or neuraminidase functions. This may include blocking of the haemagglutination function through modulation of the haemagglutinin protein.

In one embodiment, it may be preferred that the haemagglutinin-neuraminidase inhibitor is an influenza or parainfluenza haemagglutinin and/or neuraminidase inhibitor or blocker. Put another way, in one embodiment, it may be preferred that the inhibitor of haemagglutinin and/or neuraminidase functions is an inhibitor of influenza or parainfluenza haemagglutinin and/or neuraminidase functions. This may include blocking of the influenza or parainfluenza haemagglutination function and so modulation of the influenza haemagglutinin protein or parainfluenza haemagglutinin-neuraminidase protein.

A number of synthetic pathways can be employed to access the compounds of the invention. The experimental section details certain pathways by which certain inhibitors of the invention were synthesised to use as reference compounds. Relevant synthetic techniques, which may also be applied to synthesis of compounds of the first aspect, are disclosed in *Nature Scientific Reports,* 7:4507, 3 Jul. 2017; *Angew. Chem. Int. Ed.* 2015, 54, 2936-2940; *Nature Scientific Reports,* 6:24138, 7 Apr. 2016; *Med. Chem. Commun.,* 2017, 8, 130-134; *J. Med. Chem.* 2014, 57, 7613-7623; *Carbohydr. Res.* 244, 181-185 (1993); *Nature Communications,* 5:5268, 20 Oct. 2014; *Viruses,* 2019, 11, 417, 5 May 2019; *Carbohydr. Res.* 342, 1636-1650 (2007); *Bioorg. Med. Chem. Lett.* 16, 5009-5013 (2006); PCT application WO2002076971; and PCT application WO2016033660, each of which is hereby incorporated by reference in their entirety. Such techniques and synthetic approaches can be employed to access all of the compounds of the first aspect.

According to a second aspect of the invention there is provided a pharmaceutical composition comprising an effective amount of a compound of any embodiment or formulae of the first aspect, or a pharmaceutically acceptable salt thereof, and a pharmaceutically acceptable carrier, diluent and/or excipient.

Suitably, the pharmaceutical composition may be for the treatment or prophylaxis of a disease, disorder or condition caused by viral infection.

The pharmaceutical composition may include more than one compound of formula (I). When the composition includes more than one compound then the compounds may be in any ratio. The composition may further comprise known co-actives, delivery vehicles or adjuvants.

The compound of any embodiment or formulae of the first aspect is present in the pharmaceutical composition in an amount sufficient to inhibit or ameliorate the disease, disorder or condition which is the subject of treatment. Suitable dosage forms and rates of the compounds and the pharmaceutical compositions containing such may be readily determined by those skilled in the art.

Dosage forms may include tablets, dispersions, mists, aerosols, suspensions, injections, solutions, syrups, troches, capsules and the like.

A third aspect of the invention resides in a method of treating a disease, disorder or condition caused by viral infection in a patient including the step of administering an effective amount of a compound of any embodiment or formulae of the first aspect, or a pharmaceutically effective salt thereof, or the pharmaceutical composition of the second aspect to the patient.

A fourth aspect of the invention provides for a compound of any embodiment or formulae of the first aspect, or a pharmaceutically effective salt thereof, or the pharmaceutical composition of the second aspect for use in the treatment of a disease, disorder or condition caused by viral infection in a patient.

A fifth aspect of the invention provides for use of a compound of any embodiment or formulae of the first aspect, or a pharmaceutically effective salt thereof, in the manufacture of a medicament for the treatment of a disease, disorder or condition caused by viral infection.

In one embodiment of the third, fourth or fifth aspects, the disease, disorder or condition is selected from parainfluenza, influenza, croup, bronchiolitis and pneumonia. When the disease, disorder or condition is influenza then it may be influenza A, B, C or D.

In one embodiment of the third, fourth or fifth aspects, the disease, disorder or condition is an infection caused by an influenza and/or parainfluenza virus.

The infection may be caused by one or more of an influenza A virus, influenza B virus, influenza C virus, influenza D virus, parainfluenza virus, respiratory syncytial virus (RSV) and human metapneumovirus (hMPV).

When the disease, disorder or condition is parainfluenza viral infection, it may be selected from the group consisting of an hPIV-1, -2, -3 and -4 virus. These may include all viral subtypes, e.g. 4a and 4b.

When the disease, disorder or condition is caused by RSV then it may be the A and/or B subtypes, for example, hRSV-A and hRSV-B.

When the disease, disorder or condition is caused by hMPV then it may be caused by any one or more of the hMPV A1, A2, B1 and B2 subtypes Preferably, the patient is a domestic or livestock animal or a human.

A sixth aspect of the invention provides for a method of modulating viral haemagglutinin and/or neuraminidase function including the step of contacting the viral haemagglutinin-neuraminidase with a compound of any embodiment or formulae of the first aspect.

Preferably, the modulating involves inhibiting the viral haemagglutinin and/or neuraminidase functions or viral haemagglutinin-neuraminidase enzyme.

DEFINITIONS

In this patent specification, the terms 'comprises', 'comprising', 'includes', 'including', or similar terms are intended to mean a non-exclusive inclusion, such that a method or composition that comprises a list of elements does not include those elements solely, but may well include other elements not listed.

Unless defined otherwise, all technical and scientific terms used herein have the same meaning as would be commonly understood by those of ordinary skill in the art to which this invention belongs.

As used herein, "effective amount" refers to the administration of an amount of the relevant active agent sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight etc. An appropriate dosage or dosage regime can be ascertained through routine trial.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, palmoate, piperazine, pectinate and S-methyl methionine salts and the like.

The terms "substituted" and "optionally substituted" in each incidence of its use herein, and in the absence of an explicit listing for any particular moiety, refers to substitution of the relevant moiety, for example an alkyl chain or ring structure, with one or more groups selected from $C_1$-$C_6$ alkyl, $C_1$-$C_6$ haloalkyl, $C_1$-$C_6$ alkoxy, $C_1$-$C_6$ haloalkoxy (such as trifluoromethoxy, trifluoroethoxy and the like) CN, OH, oxo, $NH_2$, $NR_{28}R_{28}'$ (wherein $R_{28}$ and $R_{28}'$ are independently selected from hydrogen, optionally substituted $C_1$-$C_9$ alkyl, optionally substituted aryl, $R_{29}C{=}O$, $R_{29}SO_2$, and $R_{29}NHC{=}O$ wherein $R_{29}$ is $C_1$-$C_9$ alkyl), Cl, F, Br, I, aryl and heterocyclyl which latter two moieties may themselves be optionally substituted. When the term is used before the recitation of a number of functional groups then it is intended to apply to all of the listed functionalities unless otherwise apparent. For example, "optionally substituted amino, heterocyclic, aryl" means all of the amino, heterocyclic and aryl groups may be optionally substituted.

The term "alkyl" refers to a straight-chain or branched alkyl substituent containing from, for example, 1 to about 12 carbon atoms, preferably 1 to about 8 carbon atoms, more preferably 1 to about 6 carbon atoms, even more preferably from 1 to about 4 carbon atoms, still yet more preferably 1 or 2 carbon atoms. Examples of suitable alkyl groups include, but are not limited to, methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl and the like. The number of carbons referred to relates to the carbon backbone and carbon branching but does not include carbon atoms belonging to any substituents, for example the carbon atoms of an alkoxy substituent branching off the main carbon chain.

The term "haloalkyl", "haloalkenyl", "haloalkynyl" and the like refers to an alkyl, alkenyl, or alkynyl group in which one or more of the hydrogen atoms have been replaced with a halogen (preferably F, Cl, Br or I; even more preferably F, Cl or Br; still more preferably F or Cl). In one embodiment, less than 10%, 20%, 30%, 40%, 50%, 60%, 70%, 80% or 90% of the hydrogen atoms in the relevant group have been replaced with a halogen. In another embodiment, more than 10%, 20%, 30%, 40%, 50%, 60%, 70%, 80% or 90% of the hydrogen atoms in the relevant group have been replaced with a halogen. A haloalkyl group may include, for example, only one halogen atom, or may be a perhaloalkyl group. In some embodiments, a $C_2$-$C_6$ haloalkenyl group may especially be a $C_3$-$C_6$ haloalkenyl group. In some embodiments, a $C_2$-$C_9$ haloalkenyl group may especially be a $C_3$-$C_9$ haloalkenyl group. In some embodiments, a $C_2$-$C_6$ haloalkynyl group may especially be a $C_3$ -$C_6$ haloalkynyl group. In some embodiments, a $C_2$-$C_9$ haloalkynyl group may especially be a $C_3$ -$C_9$ haloalkynyl group.

The term "alkenyl" refers to a straight-chain or branched alkenyl substituent containing from, for example, 2 to about 12 carbon atoms, preferably 2 to about 8 carbon atoms, more preferably 2 to about 6 carbon atoms. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl, decenyl, undecenyl, dodecenyl and the like. Branched alkenyl groups may be branched at any suitable position, and exemplary branched alkenyl groups may include, for example, 2-methyl-1-pentenyl, 3-methyl-1-pentenyl, 2-methyl-2-pentenyl, 2-methyl-3-pentenyl, 2-methyl-4-pentenyl and the like. The number of carbons referred to relates to the carbon backbone and carbon branching but does not include carbon atoms belonging to any substituents, for example the carbon atoms of an alkoxy substituent branching off the main carbon chain. In some embodiments, a $C_2$-$C_6$ alkenyl group may especially be a $C_3$-$C_6$ alkenyl group. In some embodiments, a $C_2$ -$C_9$ alkenyl group may especially be a $C_3$ -$C_9$ alkenyl group.

The term "alkynyl" refers to a straight-chain or branched alkynyl substituent containing from, for example, 2 to about 12 carbon atoms, preferably 2 to about 8 carbon atoms, more preferably 2 to about 6 carbon atoms. Examples of suitable alkynyl groups include, but are not limited to, ethynyl, propynyl, butynyl, butadiynyl, pentynyl, hexynyl, heptynyl, octynyl, nonynyl, decynyl, undecynyl, dodecynyl and the like. Branched alkynyl groups may be branched at any suitable position, and exemplary branched alkynyl groups may include, for example, 3-methyl-1-pentynyl, 2-methyl-3-pentynyl, 2-methyl-4-pentynyl and the like. The number of carbons referred to relates to the carbon backbone and carbon branching but does not include carbon atoms belonging to any substituents, for example the carbon atoms of an alkoxy substituent branching off the main carbon chain. In some embodiments, a $C_2$-$C_6$ alkynyl group may especially be a $C_3$-$C_6$ alkynyl group. In some embodiments, a $C_2$-$C_9$ alkynyl group may especially be a $C_3$-$C_9$ alkynyl group.

The term "cycloalkyl" refers to a saturated non-aromatic mono-cyclic, bicyclic or tricyclic hydrocarbon. Where appropriate, the cycloalkyl group may have a specified number of carbon atoms, for example, $C_3$-$C_6$ cycloalkyl is a carbocyclic group having 3, 4, 5 or 6 carbon atoms. When more than one ring is present the rings are fused together (for example, a bicyclic ring is fused if two atoms are common to both rings). Non-limiting examples may include cyclopropyl, cyclobutyl, cyclopentyl, cyclohexyl and the like.

The term "cycloalkenyl" or "cycloalkene" refers to a cyclic hydrocarbon having at least one double bond, which is not aromatic. The cycloalkenyl ring may include a specified number of carbon atoms. For example, a 5 membered cycloalkenyl group includes 5 carbon atoms. The cycloalkenyl group may be monocyclic, bicyclic or tricyclic. When more than one ring is present the rings are fused together (for example, a bicyclic ring is fused if two atoms are common to both rings). Non-limiting examples may include cyclopentenyl and cyclopenta-1,3-dienyl.

The term "aryl" refers to an unsubstituted or substituted aromatic carbocyclic substituent, as commonly understood in the art. It is understood that the term aryl applies to cyclic substituents that are planar and comprise $4n+2\pi$ electrons, according to Hückel's Rule. C-6 aryl is preferred.

The terms "heterocyclic" and "heterocyclyl" as used herein specifically in relation to certain 'R' groups refer to a moiety obtained by removing a hydrogen atom from a ring atom of a heterocyclic compound which may have 5 to 7 atoms in the ring and of those atoms between 1 to 4 are heteroatoms, wherein said heteroatoms are independently selected from O, N and S, and wherein unless explicitly defined said ring being isolated or fused to a second ring. Heterocyclic and heterocyclyl includes aromatic heterocyclyls and non-aromatic heterocyclyls. Heterocyclic systems may be attached to another moiety via any number of carbon atoms or heteroatoms of the radical and may be both saturated and unsaturated. Heterocyclic systems may be attached to another moiety via any number of carbon atoms or heteroatoms of the radical and may be both saturated and unsaturated. Non-limiting examples of heterocyclic may be selected from pyrazole, imidazole, indole, isoindole, triazole, benzotriazole, tetrazole, pyrimidine, pyridine, pyrazine, diazine, triazine, tetrazine, pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl, thiapinyl, imidazolinyl, thiomorpholinyl, and the like. The term "heterocyclyl" may be "heterocyclic ring".

The terms "heteroaryl" or "aromatic heterocyclyl" refers to an aryl group containing from one or more (particularly one to four) non-carbon atom(s) (particularly N, O or S) or a combination thereof, which heteroaryl group is optionally substituted at one or more carbon or nitrogen atom(s). Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 5-membered heteroaryls having four heteroatoms (e.g., tetrazoles); 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g., 1,3,5- triazine); and 6-membered heteroaryls with four heteroatoms. "Substituted heteroaryl" means a heteroaryl having one or more non-interfering groups as substituents and including those defined under 'optionally substituted'. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

As used herein, terminology such as

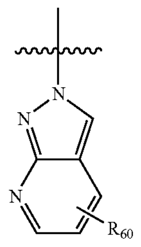

means that any number of $R_{60}$ substituents may be appended to the cyclic system (for example, up to 1, 2, 3, 4, 5, 6 or 7 substituents, as appropriate), and at any position, including on either ring (for example $R_{60}$ may be appended to the pyridyl ring and/or the diazolyl ring).

The term "protected OH" or "protected hydroxy" refers to a hydroxyl group which is protected with a common protecting group such as an acyl group, ether group or ester group including $C_1$-$C_3$ acyl, $C_1$-$C_4$ alkyl groups to form the ether or aryl, such as benzyl, forming the ether or $C_1$-$C_4$ ester.

Whenever a range of the number of atoms in a structure is indicated (e.g., a $C_1$-$C_{12}$, $C_1$-$C_{10}$, $C_1$-$C_9$, $C_1$-$C_6$, $C_1$-$C_4$, alkyl, etc.), it is specifically contemplated that any sub-range or individual number of carbon atoms falling within the indicated range also can be used. Thus, for instance, the recitation of a range of 1-12 carbon atoms (e.g., $C_1$-$C_{12}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$ -$C_8$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment for a disease or condition caused by viral infection. However, it will be understood that the aforementioned terms do not imply that symptoms are necessarily present.

References herein to "haemagglutinin-neuraminidase", "haemagglutinin-neuraminidase protein" and the like may be considered interchangeable with "haemagglutinin and/or neuraminidase functions". They may be considered to incorporate one or both of blocking of the haemagglutination function or inhibition of the neuraminidase (enzyme) function. The blocking of the haemagglutination function may therefore involve modulation, blocking or inhibition of the haemagglutinin-neuraminidase protein which may, without wishing to be bound by any theory, be one mechanism of action of the compounds described herein.

The various features and embodiments of the present invention, referred to in individual sections above apply, as appropriate, to other sections, mutatis mutandis. Consequently, features specified in one section may be combined with features specified in other sections as appropriate.

Further features and advantages of the present invention will become apparent from the Summary of the Invention section above.

The following experimental section describes in more detail the characterisation of certain of the compounds of the invention and their antiviral activity. The intention is to illustrate certain specific embodiments of the compounds of the invention and their efficacy without limiting the invention in any way.

EXPERIMENTAL

Chemistry

General Synthetic Schemes

Cyano-pyrrole analogues may be synthesised as outlined in Scheme 1 below.

Scheme 1 Synthesis of cyano-pyrrole analogues

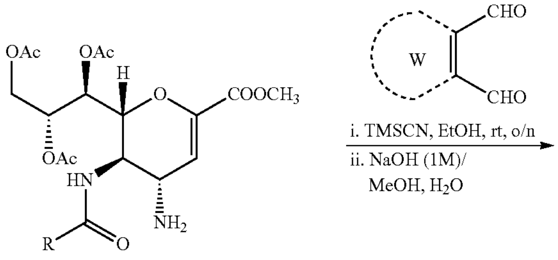

4-Amino-Neu5Ibu2en

-continued

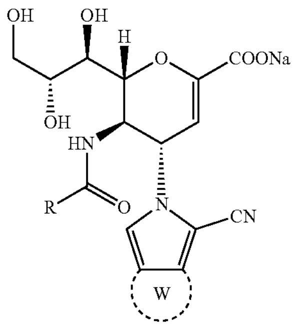

Cyano-isoindole analogues

As illustrated in Scheme 1, in step i the dialdehyde is coupled to the primary amino group, forming the cyano-pyrrole analogue, and then the OAc groups may be deprotected in a basic solution in step ii.

Diazole analogues may be synthesised as outlined in Scheme 2 below.

Scheme 2 Synthesis of diazaole analogues

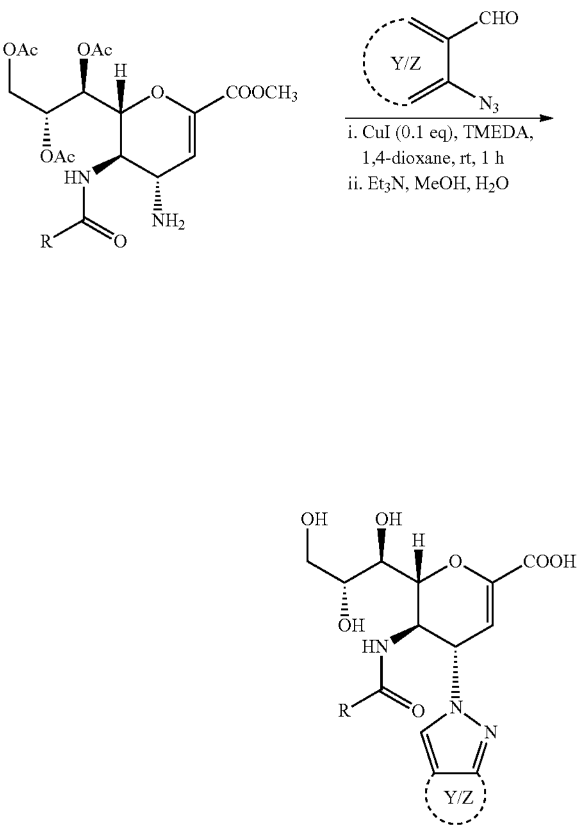

As illustrated in Scheme 2, in step i the aldehyde-azide derivative is coupled to the primary amino group, forming the diazole analogue, and then the OAc groups may be deprotected in a basic solution in step ii.

Triazole analogues may be synthesised as outlined in Scheme 3 below.

Scheme 3 Synthesis of triazole analogues

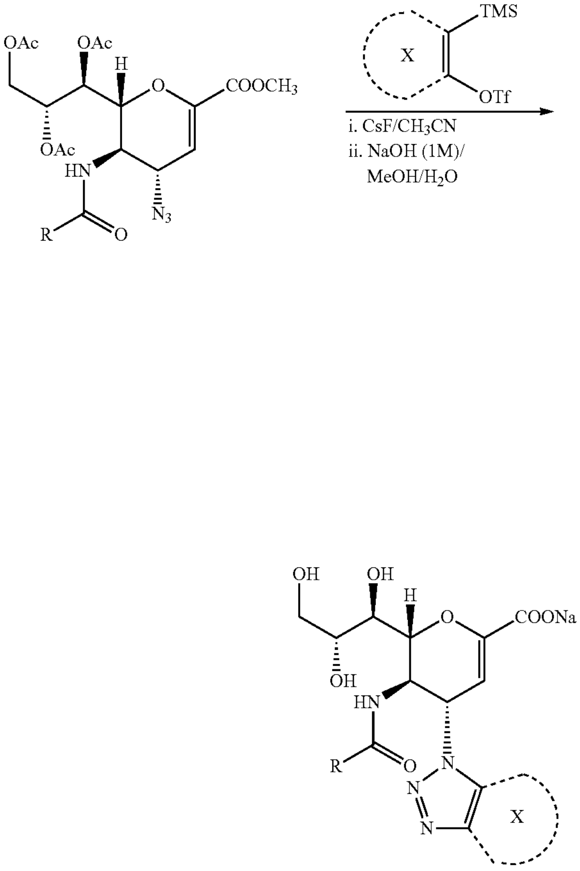

As illustrated in Scheme 3, in step i the trifluoromethanesulfonate-trimethylsilyl derivative is coupled to the azide group, forming the triazole analogue, and then the OAc groups may be deprotected in a basic solution in step ii.

General Information

Reagents and dry solvents were purchased from commercial sources and used without further purification. Anhydrous reactions were carried out under an atmosphere of argon in oven-dried glassware. Reactions were monitored using thin layer chromatography (TLC) on aluminium plates precoated with Silica Gel 60 F254 (E. Merck). Developed plates were observed under UV light at 254 nm and then visualized after application of a solution of $H_2SO_4$ in EtOH (5% v/v) followed by charring. Flash chromatography was performed on Silica Gel 60 (0.040- 0.063 mm) using distilled solvents. $^1$H and $^{13}$ C NMR spectra were recorded at 400 and 100 MHz respectively on a BrukerAvance 400 MHz spectrometer. Chemical shifts (δ) are reported in parts per million, relative to the residual solvent peak as internal reference [$CDCl_3$: 7.26 (s) for $^1$H, 77.0 (t) for $^{13}$C; $CD_3OD$: 4.78 (s) and 3.31 (pent) for $^{13,\ 49.15}$ (hept) for $^{13}$C; $D_2O$: 4.79 (s) for $^1$H]. 2D COSY and HS QC experiments were run to support assignments. Low-resolution mass spectra (LRMS) were recorded, in electrospray ionization mode, on a BrukerDaltonics Esquire 3000 ESI spectrometer, using positive mode.

Synthesis

Synthesis of IE1993-40

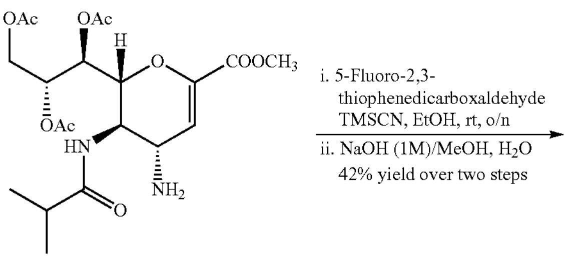

4-Amino-Neu5Ibu2en

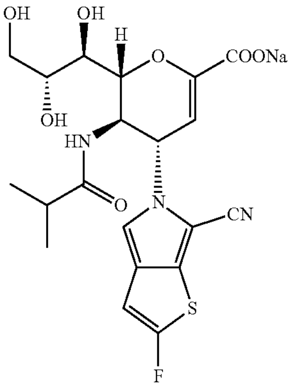

IE1993-40

To a solution of 5-fluoro-2,3-thiophenedicarboxaldehyde (17 mg, 0.109 mmol) in EtOH (1 mL) was added TMSCN (16 μL, 0.131 mmol) and the mixture was stirred at rt for 15 min. To the stirred solution was added 4-amino-Neu5Ibu2en[1] (50 mg, 0.109 mmol) in EtOH (1 ml) in a dropwise manner. The reaction mixture was stirred at rt for o/n and was then concentrated under reduced pressure and the crude product was purified by silica gel chromatography using hexane:acetone (3:1) as solvent to yield the pure protected product. To a suspension of the protected product in a (1:1) mixture of MeOH and water (2 mL) at 0° C. was added NaOH solution (1.0 M) dropwise until the pH reaches 13-14. The temperature was raised gradually to rt and the mixture was stirred at rt overnight. The solution was then acidified with Amberlite™IR-120 ($H^+$) resin (to pH=5), filtered and washed with MeOH (10 mL) and $H_2O$ (10 mL). The combined filtrate and washings were then concentrated under vacuum and the residue was diluted with distilled water (5 mL) and adjusted to pH=8.0 using 0.05 M NaOH to convert the compound to its Na-salt. The compound was then purified by reversed phase chromatography, by running it through a $C_{18}$-GracePure ™ cartridge, using 10% MeOH/water, to yield the pure product 1E1993-40 (42% yield over two steps). $^1$H NMR (400 MHz, $D_2O$): δ 0.94 (d, J =6.9 Hz, 3H), 1.01 (d, J=6.9 Hz, 3H), 2.46 (p, J=6.9 Hz, 1H), 3.62-3.71 (m, 2H), 3.92 (dd, J=12.0, 2.7 Hz, 1H), 4.01 (ddd, J=9.4, 6.4, 2.7 Hz, 1H), 4.48 (t, J=10.3 Hz, 1H), 4.58 (d, J=10.9 Hz, 1H), 5.26 (m, 1H), 5.88 (d, J=2.2 Hz, 1H), 6.71 (d, J=1.9 Hz, 1H), 7.36 (s, 1H); $^{13}$C NMR (101 MHz, $D_2O$): δ 18.18, 18.65, 35.13, 48.89, 58.89, 63.05, 68.21, 69.78, 75.43, 95.92 (d, J=14.9 Hz), 103.64, 114.52, 150.24, 165.88, 168.87 (d, J=11.1 Hz), 180.39; LRMS [$C_{20}H_{21}FN_3NaO_7S$] (m/z): (+ve ion mode) 512.0 $[M+Na]^+$.

Synthesis of the Amine Intermediate 1E1530-61

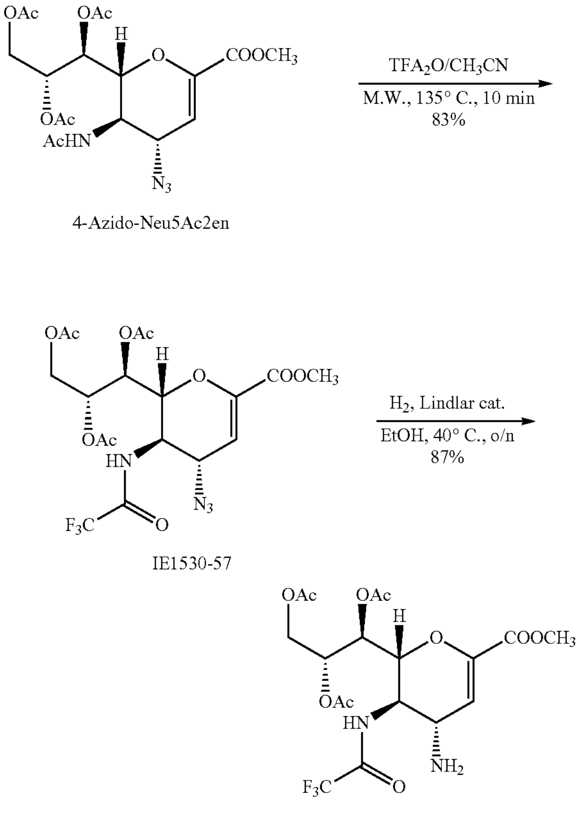

4-Azido-Neu5Ac2en

IE1530-57

IE1530-61

The 5-trifluoroacetamido analogue of 4-azido-Neu5AC2en (1E1530-57) was synthesized by microwave irradiation of 4-azido-Neu5AC2en with trifluoroacetic anhydride ($TFA_2O$) at 135° C. for 10 minutes only. The product was obtained in good purity and in high yield. Reduction of the azide group in 1E1530-57 by $H_2$ gas and in the presence of Lindlar catalyst yielded the 4-amino derivative 1E1530-61.

Methyl 7,8,9-tri-O-acetyl-2,6-anhydro-4-azido-3,4,5-trideoxy-5-(2,2,2-trifluoroacetamido)-D-glycero-D-galacto-non-2-enonate (1E1530-57)

IE1530-57

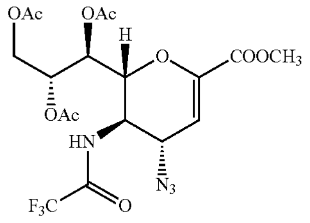

To a solution of the azide derivative 4-azido-Neu5AC2en[2] (100 mg, 0.22 mmol) in acetonitrile (0.5 mL) was added trifluoroacetic anhydride (220 μL, 1.54 mmol) and the mixture was heated in microwave reactor at 135° C. for 10 min. After cooling, MeOH (1 mL) was added, and the reaction mixture was concentrated under vacuum. The crude product was purified by silica gel chromatography using hexane:acetone (3:2) as solvent to yield pure 1E1530-57 (84 mg, 75%). $^1H$ NMR (400 MHz, $CDCl_3$): δ 2.05 (s, 3H), 2.08 (s, 3H), 2.14 (s, 3H), 3.82 (s, 3H), 3.92 (q, J=8.9 Hz, 1H), 4.19 (dd, J=12.5, 6.5 Hz, 1H), 4.47-4.57 (m, 2H), 4.66 (dd, J=12.5, 2.7 Hz, 1H), 5.31 (td, J=6.0, 5.4, 2.8 Hz, 1H), 5.39 (dd, J=5.2, 2.3 Hz, 1H), 6.02 (d, J=2.7 Hz, 1H), 7.22 (d, J=8.8 Hz, 1H); $^{13}C$ NMR (101 MHz, $CDCl_3$): δ 20.61, 20.66, 20.87, 49.05, 52.77, 57.03, 61.79, 67.54, 70.84, 75.01, 107.05, 115.39 (q, J=288.0 Hz), 145.25, 157.66 (d, J=38.3 Hz), 161.25, 170.50, 170.65, 170.92; LRMS [$C_{18}H_{21}F_3N_4O_{10}$] (m/z): (+ve ion mode) 533.2 $[M+Na]^+$

Methyl 7,8,9-tri-O-acetyl-4-amino-2,6-anhydro-3,4,5-trideoxy-5-(2,2,2-trifluoroacetamido)-D-glycero-D-galacto-non-2-enonate (1E1530-61)

IE1530-61

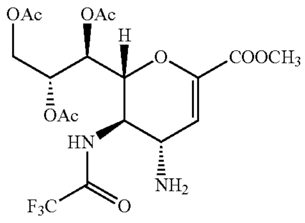

To a solution of the azide derivative 1E1530-57 (200 mg, 0.41 mmol) in ethanol (5 mL) was added Lindlar catalyst (20 mg) and the reaction mixture was stirred under $H_2$ atmosphere at rt o/n. Upon reation completion, the reaction mixture was filtered through celite bed, followed by washing with ethanol (50 mL). The combined filtrate and washing were combined and concentrated under vacuum to yield crude 1E1530-61 (quantitative yield) that was of sufficient purity to be used in the next step without further purification. LRMS [$C_{18}H_{26}N_2O_{10}$] (m/z): (+ve ion mode) 507.2 $[M+Na]^+$

Synthesis of $JC_{2001}$-48

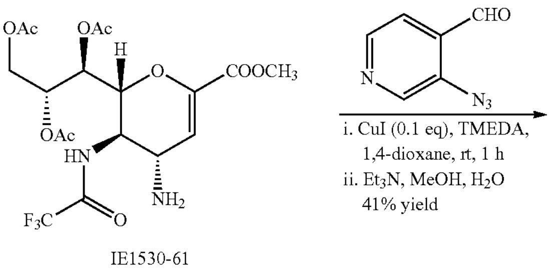

IE1530-61

-continued

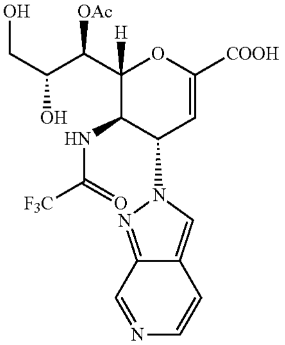

JC2001-48

2,6-Anhydro-3,4,5-trideoxy-5-(2,2,2-trifluoroacetamido)-4-(2H-pyrazolo[3,4-c]pyridin-2-yl)-D-glycero-D-galacto-non-2-enonic Acid To a solution of 1E1530-61 (50 mg, 0.103 mmol) in 1,4-dioxane (2 ml) were added 4 Å molecular sieves (100 mg) and 3-azidoisonicotinaldehyde (18 mg, 0.124 mmol) followed by TMEDA (16 μL, 0.103 mmol) and CuI (2 mg, 0.01 mmol). The reaction mixture was stirred at rt for 1 h and was then filtered over celite and the filtration bed was washed with EtOAc. The combined filtrate and washing were removed under reduced pressure and the crude product was purified by silica gel chromatography using Hexane: acetone (2:1) as solvent to yield the pure protected indazole. To a suspension of the protected indazole in a (1:1) mixture of MeOH and water (2 mL) at 0° C. was added $Et_3N$ (1 mL) dropwise. The temperature was raised gradually to rt and the mixture was stirred at rt for 2 nights. The solution was concentrated under vacuum and purified by silica gel chromatography using EtOAc/MeOH/$H_2O$ (7:2:1) to yield the final deprotected product $JC_{2001}$-48 in an overall yield of 41% over two steps. $^1H$ NMR (400 MHz, $D_2O$): δ 3.63-3.75 (m, 2H), 3.92 (dd, J=12.0, 2.7 Hz, 1H), 4.06 (ddd, J=9.4, 6.5, 2.7 Hz, 1H), 4.67 (m, 1H), 4.74 (d, J=11.0 Hz, 1H), 5.67 (dd, J=9.4, 2.3 Hz, 1H), 6.01 (d, J=2.2 Hz, 1H), 7.79 (d, J=6.0 Hz, 1H), 8.08 (s, 1H), 8.56 (s, 1H), 9.16 (s, 1H); $^{13}C$ NMR (101 MHz, $D_2O$): δ 49.93, 62.24, 63.02, 68.13, 69.68, 74.90, 102.34, 115.30 (d, J=286.4 Hz), 115.71, 119.31 (d, J=52.9 Hz), 124.38, 124.97, 135.69, 142.32, 150.48, 158.44 (d, J=38.2 Hz), 168.63; LRMS [$C_{17}H_{17}F_3N_4O_7$] (m/z): (−ve ion mode) 444.6 $[M-Na]^-$.

Synthesis of $JC_{2001}$-49

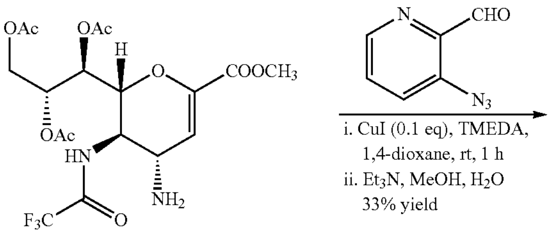

IE1530-61

-continued

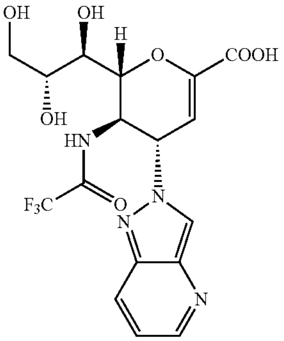

JC2001-49

2,6-Anhydro-3,4,5-trideoxy-5-(2,2,2-trifluoroacetamido)-4-(2H-pyrazolo[4,3-b]pyridin-2-yl)-D-glycero-D-galacto-non-2-enonic Acid The synthesis of $JC_{2001}$-49 followed a similar procedure to that employed for the synthesis of $JC_{2001}$-48 using methyl 3-azidopicolinaldehyde. The protected indazole was purified by silica gel chromatography using hexane:acetone (3:2) and the final deprotected product $JC_{2001}$-49 was purified by silica gel chromatography using EtOAc/MeOH/$H_2O$ (7:2:1) to yield the final indazole in an overall yield of 33% over two steps. $^1H$ NMR (400 MHz, $D_2O$): δ 3.64-3.73 (m, 2H), 3.93 (dd, J=12.0, 2.7 Hz, 1H), 4.06 (ddd, J=9.3, 6.4, 2.6 Hz, 1H), 4.66 (dd, J=10.9, 9.4 Hz, 1H), 4.73 (dd, J=10.9, 1.4 Hz, 1H), 5.60 (dd, J=9.5, 2.2 Hz, 1H), 6.02 (d, J=2.2 Hz, 1H), 7.43 (dd, J =8.8, 4.1 Hz, 1H), 8.16 (d, J=8.8 Hz, 1H), 8.57 (m, 1H), 8.63 (s, 1H); $^{13}C$ NMR (101 MHz, $D_2O$): δ 49.84, 62.10, 63.03, 68.17, 69.70, 74.89, 102.64, 115.32 (d, J=286.5 Hz), 122.57, 124.47, 126.23, 136.78, 141.86, 148.69, 150.37, 158.40 (d, J=38.2 Hz), 168.71; LRMS [$C_{17}$H17F3$N_4O_7$] (m/z): −ve ion mode) 444.7 $[M-Na]^{31}$ .

Synthesis of RP1967-89

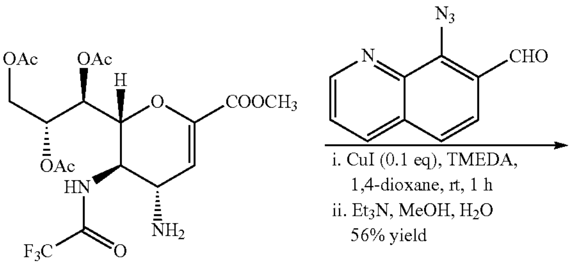

IE1530-61

-continued

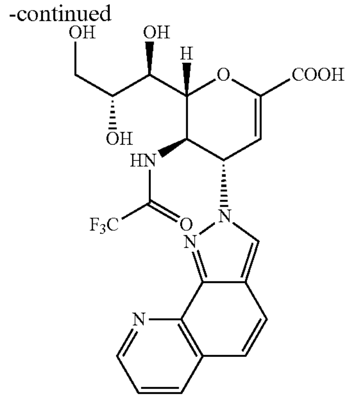

RP1967-89

2,6-Anhydro-3,4,5-trideoxy-5-(2,2,2-trifluoroacetamida)-4-(2H-pyrazolo[4,3-h]quinolin-2-yl)-D-glycero-D-galacto-non-2-enonic Acid The synthesis of RP1967-89 followed a similar procedure to that employed for the synthesis of $JC_{2001}$-48 using 8-azido-quinoline-7-carbaldehyde. The protected indazole was purified by silica gel chromatography using hexane:acetone (3:2) and the final deprotected product RP1967-89 was purified by silica gel chromatography using EtOAc/MeOH/$H_2O$ (7:2:1) to yield the final indazole in an overall yield of 56% over two steps. $^1$H NMR (400 MHz, $CD_3OD$): δ 3.58 (d, J=9.4 Hz, 1H), 3.68 (dd, J=11.5, 5.6 Hz, 1H), 3.86 (dd, J=11.5, 2.9 Hz, 1H), 3.97 (ddd, J=9.0, 5.6, 2.8 Hz, 1H), 4.71 (d, J=11.0 Hz, 1H), 4.78 (t, J=10.2 Hz, 1H), 5.70 (dd, J=9.7, 2.1 Hz, 1H), 5.88 (d, J=2.2 Hz, 1H), 7.39 (d, J=9.0 Hz, 1H), 7.57 (dd, J=8.1, 4.6 Hz, 1H), 7.70 (d, J=8.9 Hz, 1H), 8.28 (dd, J=8.2, 1.6 Hz, 1H), 8.35 (s, 1H), 8.78 (dd, J=4.6, 1.6 Hz, 1H); $^{13}$C NMR (101 MHz, $CD_3OD$): δ 49.84, 61.14, 63.48, 68.80, 69.93, 75.16, 101.87, 115.71 (d, J=287.2 Hz), 120.07, 121.65, 121.71, 121.85, 123.71, 127.88, 136.58, 141.77, 145.32, 147.77, 150.76, 157.40 (d, J=37.4 Hz); LRMS [$C_{21}$, $H_{19}$,$F_3N_4O_7$] (m/z): −ve ion mode) 494.9 $[M-H]^-$.

Synthesis of IE1963-113a and IE1963-113b

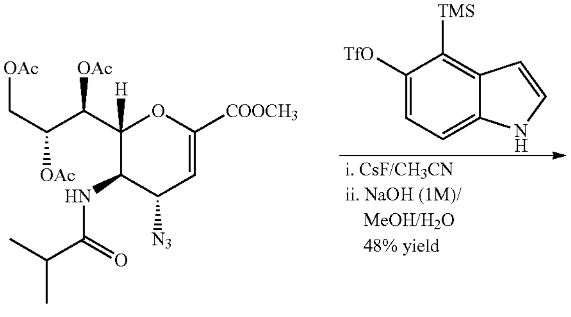

4-azido-Neu5Ibu2en

-continued

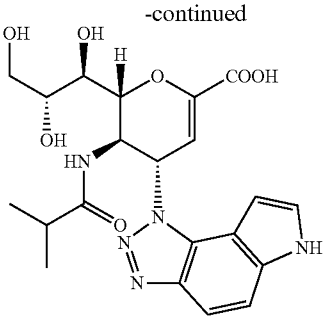

+

IE1963-113a

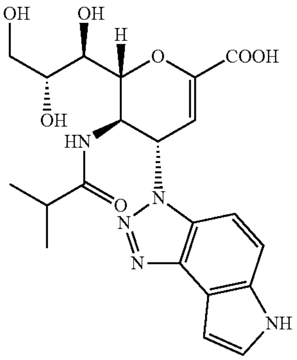

IE1963-113b

To a solution of the 4-azido-Neu5Ibu2en (60 mg, 0.124 mmol) in anhydrous $CH_3CN$ (2 mL) was added 4-(trimethylsilyl)-1H-indol-5-yl trifluoromethanesulfonate (63 mg, 0.186 mmol) and cesium fluoride (38 mg, 0.248 mmol). The reaction mixture was stirred at rt for 48 h and was then poured into a saturated aq solution of $NaHCO_3$. The resulted mixture was extracted with EtOAc (30×2). The combined organic extracts were washed with brine solution, dried over anhydrous $Na_2SO_4$ and then concentrated in vacuum. Purification by silica gel chromatography using hexane:acetone (3:2) yielded a mixture of the two benzotriazole isomers. To a suspension of the protected benzotriazoles derivative in a (1:1) mixture of MeOH and water (2 mL) at 0° C. was added NaOH solution (1.0 M) dropwise until the pH reaches 13-14. The temperature was raised gradually to rt and the mixture was stirred at rt overnight. The solution was then acidified with Amberlite™IR-120 ($H^+$) resin (to pH=5), filtered and washed with MeOH (10 mL) and $H_2O$ (10 mL). The combined filtrate and washings were then concentrated under vacuum and the residue was diluted with distilled water (5 mL) and adjusted to pH=8.0 using 0.05 M NaOH to convert the compound to its Na-salt (48% cobmined isomers yield over two steps). The deprotected isomers were then separated using HPLC.

IE1963-113a: $^1$H NMR (400 MHz, $D_2O$): δ 0.72 (m, 6H), 2.08 (m, 1H), 3.62-3.76 (m, 2H), 3.94 (dd, J=12.1, 2.7 Hz, 1H), 4.09 (ddd, J=9.3, 6.3, 2.7 Hz, 1H), 4.75 (s, 2H), 6.07 (dd, J=14.8, 6.3 Hz, 2H), 6.91 (s, 1H), 7.51 (d, J=3.1 Hz, 1H), 7.63 (d, J=9.2 Hz, 1H), 7.69 (d, J=9.1 Hz, 1H).

IE1963-113b: $^1$H NMR (400 MHz, $D_2O$): δ 0.60 (d, J=6.9 Hz, 3H), 0.81 (d, J=6.9 Hz, 3H), 2.22 (p, J=6.9 Hz, 1H), 3.63 ? 3.74 (m, 2H), 3.93 (dd, J=12.0, 2.7 Hz, 1H), 4.06 (ddd, J=9.3, 6.3, 2.7 Hz, 1H), 4.73 (d, J=9.9 Hz, 2H), 5.94 (d, J=8.7 Hz, 1H), 6.05 (d, J=2.3 Hz, 1H), 7.04 (dd, J =3.0, 0.8 Hz, 1H), 7.45 (d, J=9.0 Hz, 1H), 7.53 (d, J=3.1 Hz, 1H), 7.74 (dd, J=8.9, 0.8 Hz, 1H); $^{13}$C NMR (101 MHz, $D_2O$): δ 18.06, 18.28, 34.86, 47.10, 58.88, 63.08, 68.22, 69.80, 75.51, 99.21, 102.91, 103.82, 115.25, 115.38, 125.69, 128.96, 132.59, 139.08, 150.13, 168.90, 180.32.

Biology

Cells and Virus

LLC-MK2 cells (Rhesus monkey kidney, ATCC CCL-7) and MA104 cells (Rhesus monkey kidney, ATCC CRL-2378.1) were cultured in Eagle's minimal essential medium (EMEM) supplemented with 1% Glutamine (200 mM) and 2% of foetal bovine serum (FBS). During hPIV-3 (LLC-MK2) and hPIV-1 (MA104) infection and post-infection incubation, LLC-MK2 and MA104 cells were maintained in EMEM supplemented only with 1% glutamine (no FBS). All cell lines were incubated at 37° C. in a humidified atmosphere of 5% $CO_2$. hPIV-3 (strain C-243) and hPIV-1 (strain C-35) were obtained from the American Type Culture Collection (ATCC). hPIV-3 (strain CI002) is clinical isolate obtained from the Gold Coast University Hospital. The viruses were propagated in LLC-MK2 cells for hPIV-3 and in MA104 cells for hPIV-1 with EMEM supplemented with only glutamine at 35 ° C. in a humidified atmosphere of 5% CO 2 . Media was also supplemented with 1.6% of TrypLE Express (Gibco) for production of hPIV-1 and hPIV-3 clinical isolate. Virus-containing culture supernatant was collected 3 to 4 days post-infection, while monitoring cytopathic effects, and clarified from cell debris by centrifugation (3,000 RCF for 15 min). Virus was concentrated at least 10 times using 30 kDa Amicon Ultra filter unit for use in Haemagglutination Inhibition (HI) assays. Neuraminidase Inhibition (N1) assays used virus that was PEG-precipitated and then purified as described below. Clarified hPIV-3 or hPIV-1 supernatant was mixed with PEG6000 (8% final concentration) and NaCl (0.4 M final concentration) then incubated overnight at 4° C. under gentle agitation. PEG6000/hPIV complex was pelleted by centrifugation at 3,000 RCF for 30 min at 4° C. The supernatant was discarded and a volume of GNTE buffer (200 mM glycine, 200 mM NaCl, 20 mMTris-HCl, 2 mM EDTA, pH 7.4) corresponding to at least 1:40 of the initial virus suspension volume was used to resuspend the pellet overnight at 4 ° C. The virus suspension was homogenized by up and down pipetting followed by a mechanical disruption of the remaining virus aggregates using a douncer with "tight" pestle. The hPIV-3 or hPIV-1 homogenate was loaded on top of a 30%-60% non-linear sucrose gradient prepared in GNTE buffer and centrifuged at 100,000 RCF for 2 h 30 min at 4° C. without brake for deceleration. The virus was concentrated at the 30%-60% sucrose interface and then collected and stored at −4° C. for Nl assays.

hPIV HN Inhibitors

Compounds were provided as a lyophilized powder and then solubilized in sterile water or DMSO to generate a 10 mM stock solution. Solutions were sonicated for 15 min to allow complete dissolution. The stock solution was stored in an amber glass vial at −20° C. and freshly diluted in appropriate buffer before use.

Haemagglutination Inhibition Assay

The HN inhibitors were assessed in duplicate in a U-bottom 96 well plate assay. Compounds were diluted in PBS as a 4× solution for each concentration tested (25 μL/well, 1× final). Each dilution was mixed with 4 haemagglutination units (HAU) of hPIV-3 or hPIV-1(25 μL/well, 1 HAU final) and incubated for 20 min at room temperature. An equivalent volume (50 μL/well) of 1% human red blood cells (h-RBC) was added to each well. The plate was then incubated for 1 h at room temperature (22-23° C.) before reading the extent of haemagglutination. The haemagglutination $IC_{50}$ is considered as the concentration of inhibitor that reduced the haemagglutinin activity (agglutination) by 50% compared to those of a 1 HAU of non-treated virus suspension.

Neuraminidase Inhibition Assay

Purified hPIV-3 or hPIV-1, inhibitors and MUN were prepared and diluted in NA Reaction Buffer [NaOAc 50 mM, $CaCl_2$ 5 mM, pH 4.6 (hPIV-3) or 5.0 (hPIV-1)]. Neuraminidase assay, employing different hPIV-3 or hPIV-1 dilutions, were initially measured to determine the lowest virus concentration to be used in the assays. The neuraminidase assays were performed with enough purified virus to obtain a maximal fluorescence signal at least 5 times higher than the background for the experiment to be considered statistically significant. Neuraminidase inhibition (N1) assays were done in triplicate in 384 well black plate. For each concentration tested, 2 μL of purified hPIV and 4 μL of 2.5× inhibitor solution (1× final) was added to each well. The plate was kept at room temperature for 20 min before 4 μL of 5 mM 2'-(4-Methylumbelliferyl)-α-D-N-acetyl-neuraminic acid (MUN) (2 mM final) was added to each well and then the plate incubated at 37° C. for 30 min with agitation (1100 rpm). The enzymatic reaction was stopped by the addition of 50 μl of glycine buffer (glycine 0.25 M, pH 10.4) to each well. A negative control was included by the addition of MUN to virus and then the enzymatic reaction stopped at t=0 min. Relative fluorescence (RF) was measured with a Tecan Infinite M200 Pro. Data were processed by background subtraction (negative control RF) and then analysed with GraphPadPrism to calculate $IC_{50}$ values (nonlinear regression (curve fit), Dose-response - inhibition, 3 or 4 parameter logistic). The concentration of inhibitor that reduced neuraminidase activity (relative fluorescence) by 50% compared to those of a non-treated virus suspension was considered to be the neuraminidase $IC_{50}$ value.

In Situ Enzyme-Linked Immunosorbent Assay (ELISA)

In situ ELISA is a useful technique to evaluate virus growth inhibition. It measures, in one step, the expression level of hPIV-3 HN at the cell surface of an infected LLC-MK2 cell monolayer. The expression level is directly correlated to the ability of a non-immobilized virus to infect and re-infect target cells. Infection was performed with 200 FFU/well on a confluent LLC-MK2 cell monolayer seeded in a 96 well plate. Infection with hPIV-3 strains $C_{243}$ or CI002 was done in triplicate and continued for 1 h at 37° C. with gentle agitation every 15 min. Compounds were diluted at a final concentration from 250 mM to 2.5 nM as a 10-fold dilution series. Inocula were removed and replaced with 100 μL/well of each respective compound dilution. A positive control for infection was incorporated by the use of identical experimental conditions, minus inhibitor. Infected cell monolayers were kept for 36-40 h at 35° C., 5% $CO_2$ for virus proliferation. Virus was inactivated and cells fixed by the direct addition of 100 μL of 7.4% formaldehyde/PBS (3.7% final). The plate was maintained at room temperature for 15 min and then washed 3 times for 5 min with PBS. Endogenous peroxidases were then inactivated by treatment with 0.3%

$H_2O_2$/1% IGEPAL in PBS for 30 min at 37° C. The cell monolayers were washed and incubated with mouse monoclonal IgG anti-hPIV-3HN (Fitzgerald, clone# M02122321 , 2.0 mg/mL) at 1 μg/mL in 5% milk/PBS for 1 h at 37° C. The wells were washed 3 times for 5 min with 0.02% Tween20/PBS. Goat anti-Mouse-lgG(H+L)-HRP conjugate (BioRad, #1706516), diluted at 1:4000 in 5% milk/PBS, was added to each well and incubated for 1 h at 37° C. Cell monolayers were washed with 0.02% Tween20/PBS and then rinsed twice with PBS. BD OptEIA TMB substrate was added to each well (50 μL) and the plate was then incubated at 37° C. The enzymatic reaction was stopped after 3-5 min by the addition of 25 μL, of 0.6 M of $H_2SO_4$ per well. Raw data were obtained by reading the absorbance of each well at 450 nm using a xMarkTM Microplate Absorbance Spectrophotometer. Final absorbance values were obtained by subtracting the absorbance of the negative control (non-infected cells) from the other absorbance readings. The data were analysed with GraphPad Prism4 to calculate $IC_{50}$ values (nonlinear regression (curve fit), Dose response—inhibition, 3 or 4 parameter logistic). The virus growth $IC_{50}$ value was considered as the concentration of inhibitor that reduced the absorbance at 450 nm by 50%, compared to a non-treated infected cell monolayer.

TABLE 1

Biological evaluation of compounds against hPIV-1 and hPIV-3 HN functions and viral growth. $IC_{50}$ values are presented in bold and are expressed in μM.

| Compound | Haemagglutination $IC_{50}$ (μM) | Neuraminidase $IC_{50}$ (μM) | Viral Growth $IC_{50}$ (μM) |
|---|---|---|---|
| 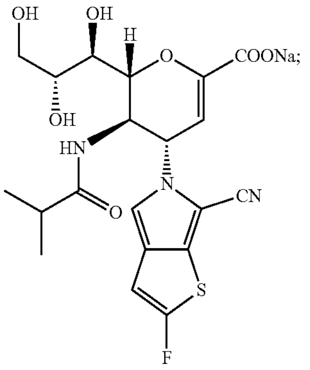<br>RE1993-40 | 0.735 ± 0.259<br>(hPIV-3 C243, n = 4)<br>0.82<br>(hPIV-3 CI002, n = 1)<br>22.22<br>(hPIV-1 C35, n = 1) | 1.145 ± 0.021<br>(hPIV-3 C243, n = 2)<br>2.713 ± 0.454<br>(hPIV-3 CI002, n = 3)<br>5.407 ± 1.317<br>(hPIV-1 C35, n = 3) | 3.217 ± 0.726<br>(hPIV-3 C243, n = 3)<br>3.963 ± 0.624<br>(hPIV-3 CI002, n = 3) |
| 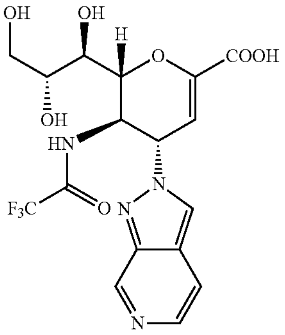 [SMILES: O=C(O)C1=C[C@H](n2cc3ccncc3n2)[C@@H](NC(=O)C(F)(F)F)[C@H]([C@H](O)[C@H](O)CO)O1]<br>JC2001-48 | 13.1<br>(hPIV-3 C243, n = 1)<br>4.94<br>(hPIV-3 CI002, n = 1)<br>0.27<br>(hPIV-1 C35, n = 1) | 21.5<br>(hPIV-3 C243, n = 1)<br>29.223 ± 6.863<br>(hPIV-3 CI002, n = 1)<br>1.707 ± 0.542<br>(hPIV-1 C35, n = 3) | 54.503 ± 16.075<br>(hPIV-3 C243, n = 4)<br>8.477 ± 2.22<br>(hPIV-3 CI002, n = 3) |
| 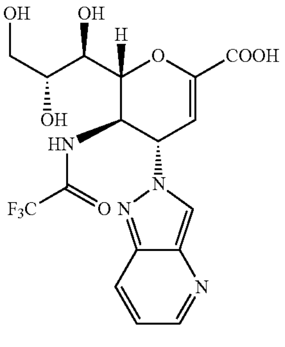 [SMILES: O=C(O)C1=C[C@H](n2cc3ncccc3n2)[C@@H](NC(=O)C(F)(F)F)[C@H]([C@H](O)[C@H](O)CO)O1]<br>JC2001-49 | 13.1<br>(hPIV-3 C243, n = 1)<br>4.94<br>(hPIV-3 CI002, n = 1)<br>14.82<br>(hPIV-1 C35, n = 1) | 8.33 ± 1.245<br>(hPIV-3 C243, n = 2)<br>15.09 ± 0.177<br>(hPIV-3 CI002, n = 3)<br>23.217 ± 1.603<br>(hPIV-1 C35, n = 3) | 26.9<br>(hPIV-3 C243, n = 1)<br>11.537 ± 3.621<br>(hPIV-3 CI002, n = 3) |

TABLE 1-continued

Biological evaluation of compounds against hPIV-1 and hPIV-3 HN functions and viral growth. $IC_{50}$ values are presented in bold and are expressed in μM.

| Compound | Haemagglutination $IC_{50}$ (μM) | Neuraminidase $IC_{50}$ (μM) | Viral Growth $IC_{50}$ (μM) |
|---|---|---|---|
| 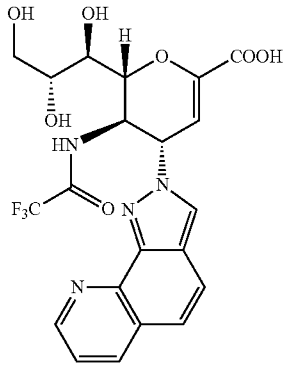 [SMILES: O=C(O)C1=C[C@H](n2cc3ccc4cccnc4c3n2)[C@@H](NC(=O)C(F)(F)F)[C@H]([C@H](O)[C@H](O)CO)O1] RP1967-89 | 3.0 (hPIV-3 C243, n = 1) 4.94 (hPIV-3 CI002, n = 1) >200 (hPIV-1 C35, n = 1) | 5.523 ± 0.983 (hPIV-3 C243, n = 3) 19.907 ± 1.953 (hPIV-3 CI002, n = 3) 88.87 ± 17.432 (hPIV-1 C35, n = 4) | 9.67 (hPIV-3 C243, n = 1) 4.997 ± 1.849 (hPIV-3 CI002, n = 3) |
| 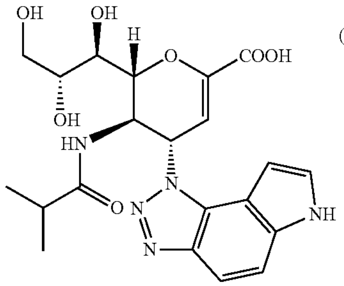 IE1963-113a | 36.7 (hPIV-3 C243, n = 1) | 16.967 ± 0.764 (hPIV-3 C243, n = 3) 34.85 (hPIV-3 CI002, n = 1) 6.33 (hPIV-1 C35, n = 1) | 111.333 ± 9.292 (hPIV-3 C243, n = 3) 42.567 ± 34.324 (hPIV-3 CI002, n = 3) |
| 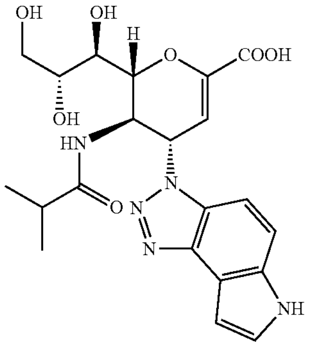 [SMILES: CC(C)C(=O)N[C@H]1[C@H]([C@H](O)[C@H](O)CO)OC(C(=O)O)=C[C@@H]1n1nnc2c3cc[nH]c3ccc21] IE1963-113b | 3.0 (hPIV-3 C243, n = 1) | 5.14 ± 0.777 (hPIV-3 C243, n = 3) 17.13 (hPIV-3 CI002, n = 1) 8.4 (hPIV-1 C35, n = 1) | 24.367 ± 3.35 (hPIV-3 C243, n = 3) 8.697 ± 5.03 (hPIV-3 CI002, n = 3) |

n: number of experiment repeats.

Standard deviation is reported next to the IC50 value when n > 1.

Structural Biology

Recombinant HN Expression and Purification:

The HN protein was expressed using the Bac-to-Bac® baculovirus expression system (Invitrogen, Carlsbad, CA) based on a substantially modified literature procedure. Thus, the nucleotide sequence for a honeybee melittin signal peptide (HBM) was added downstream to the sequence encoding for the HN ectodomain (amino acids 125 to 572). This sequence (HBM+HN) was codon optimised for expression in Spodoptera frugiperda cells (Sf9) and ordered directly through the DNA2.0 gene synthesis service (DNA2.0, Menlo Park, CA) as a gene named HBM-HNhPIV-3opt. HBM- HNhPIV-3opt was amplified by PCR and ligated into a pFastBac/CT-TOPO® vector that provides an additional C-terminal 6-histidine tag (His-Tag) for purification and detection purposes.

The generation and amplification of recombinant baculovirus containing HBM-HNhPIV-3opt were performed according to the manufacturer's instructions. Sf9 cells (Invitrogen), cultured in Insect-XPRESS protein free insect cell medium (Lonza), were infected with high MOI of HBM-HNhPIV¬-3opt baculovirus. Four days post-infection the supernatant, containing recombinant HN, was collected to yield the highest protein expression. The supernatant was clarified by centrifugation (3,000 RCF for 15 min) to remove cell debris and then purified on a HisTrap excel 5 mL column (GE Healthcare life sciences, Buckinghamshire, England) following the manufacturer's protocol. Recombinant HN was eluted with 500 mM imidazole solution and collected fractions were assessed for their neuraminidase enzymatic activity. The most active fractions were pooled and concentrated with a 10 kDa Amicon Ultra filter unit (Millipore) to a final volume of 800 μL. An additional purification step was performed that employed fast protein liquid chromatography (Amersham Biosciences) over a Superdex 75 gel filtration column (GE Healthcare) at 4° C. and 1 mL fractions were collected with a Frac-920. Protein-containing fractions, as determined by monitoring fraction collection at 280 nm, were assessed for their neuraminidase enzymatic activity as well as subjected to SDS-PAGE. Purified and concentrated recombinant HN protein was stored at 4° C.

Crystallisation, Data Collection and Structure Determination:

hPIV-3 HN complexes were prepared by co-crystallisation (with compounds IE-1993-40, $JC_{2001}$-48, and RP1967-89) where the 4 mg/mL hPIV¬-3 HN protein stock solution was preincubated with a final concentration of 1.5 mM inhibitor in 0.1 M citrate buffer pH 4.6, 0.2 M $(NH_4)_2SO_4$ and 10% PEG 3000 for 30 min. Crystallization trials were set up as 2 μL preincubated stock solution using the hanging drop vapour diffusion method. The drop was equilibrated against a 500 μL reservoir (0.1 M citrate buffer pH 4.6, 0.2 M $(NH_4)_2SO_4$ and 10% or 15% PEG 3000). The crystals were mounted in nylon loops (Hampton Research) and flash frozen at 100 K in a cryoprotectant solution containing 20% glycerol in addition to the precipitant solution.

X-ray diffraction data were collected on the MX1 and MX2 beamlines at the Australian Synchrotron using the Blu-Ice software. The datasets were processed using XDS 3 and scaled using Aimless in the CCP4 suite.[4] The structures were solved by molecular replacement using Phaser and the apo hPIV3-HN model (PDB ID: 4XJQ)[5] as template. The models were refined using Phenix.Refine,[6] and structure validation was performed using MolProbity.[7] Structure analyses were performed using Coot, 8 and PyMOL (http://www.pymol.org/; DeLano Scientific LLC).

REFERENCES

1 El-Deeb, I. M.; Guillon, P.; Winger, M.; Eveno, T.; Haselhorst, T.; Dyason, J. C.; von Itzstein, M., Exploring human parainfluenza virus type-1 hemagglutinin-neuraminidase as a target for inhibitor discovery. *J. Med. Chem.* 2014, 57, 7613-23. https://pubs.acs.org/doi/10.1021/jm500759v.

2 Lu, Y.; Gervay-Hague, J., Synthesis of C-4 and C-7 triazole analogs of zanamivir as multivalent sialic acid containing scaffolds. *Carbohydr. Res.* 2007, 342 (12-13), 1636-50 .https://doi.org/10.1016/j.carres.2007.06.002.

3 Kabsch, W. XDS. *Acta Crystallogr. D Biol. Crystallogr.* 2010, 66 (Pt 2), 125-132. https://doi.org/10.1107/S0907444909047337.

4 Potterton, L.; Agirre, J.; Ballard, C.; Cowtan, K.; Dodson, E.; Evans, P. R.; Jenkins, H. T.; Keegan, R.; Krissinel, E.; Stevenson, K.; Lebedev, A.; McNicholas, S. J.; Nicholls, R. A.; Noble, M.; Pannu, N. S.; Roth, C.; Sheldrick, G.; Skubak, P.; Turkenburg, J.; Uski, V.; von Delft, F.; Waterman, D.; Wilson, K.; Winn, M.; Wojdyr, M. CCP4i2: The New Graphical User Interface to the CCP4 Program Suite. *Acta Crystallogr. D Struct. Biol.* 2018, 74 (Pt 2), 68-84. https://doi.org/10.1107/S2059798317016035.

5 Dirr, L.; El-Deeb, I. M.; Guillon, P.; Carroux, C. J.; Chavas, L. M. G.; von Itzstein, M. The Catalytic Mechanism of Human Parainfluenza Virus Type 3 Haemagglutinin-Neuraminidase Revealed. *Angew. Chem. Int. Ed.* 2015, 54 (10), 2936-2940. http s ://doi .org/10.1002/anie.201412243 .

6 Adams, P. D.; Afonine, P. V.; Bunkóczi, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. PHENIX: A Comprehensive Python-Based System for Macromolecular Structure Solution. *Acta Crystallogr. D Biol. Crystallogr.* 2010, 66 (2), 213-221. https://doi.org/10.1107/S0907444909052925.

7 Chen, V. B.; Arendall, W. B.; Headd, J. J.; Keedy, D. A.; Immormino, R. M.; Kapral, G. J.; Murray, L. W.; Richardson, J. S.; Richardson, D. C. MolProbity: All-Atom Structure Validation for Macromolecular Crystallography. *Acta Crystallogr. D* 2010, 66 (1), 12-21. https://doi.org/10.1107/S0907444909042073.

8 Emsley, P.; Cowtan, K. Coot: Model-Building Tools for Molecular Graphics. *Acta Crystallogr. D Biol. Crystallogr.* 2004, 60 (Pt 12 Pt 1), 2126-2132. https://doi.org/10.1107/S0907444904019158.

The invention claimed is:

1. A compound of formula (I), or a pharmaceutically acceptable salt thereof:

Formula (I)

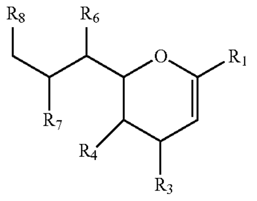

wherein $R_1$ is selected from the group consisting of COOH, or a salt thereof, $C(O)NR_9R_{10}$, and $C(O)OR_{11}$ wherein $R_9$, $R_{10}$ and $R^{11}$ are independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl and optionally substituted heterocyclyl;

$R_3$ is selected from the group consisting of:

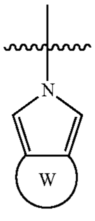 , 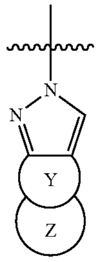 and 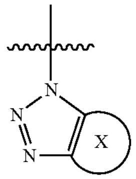

wherein ring W, together with the carbon atoms to which it is attached, form an optionally substituted monocyclic heterocyclic ring, an optionally substituted monocyclic heteroaryl ring, an optionally substituted fused bicyclic heterocyclic ring or an optionally substituted fused bicyclic heteroaryl ring;

wherein:

(i) ring Y, together with the carbon atoms to which it is attached, form an optionally substituted monocyclic heterocyclic ring or an optionally substituted monocyclic heteroaryl ring; and ring Z, together with two ring atoms of ring Y, form an optionally substituted monocyclic heterocyclic ring, an optionally substituted monocyclic heteroaryl ring, an optionally substituted monocyclic cycloalkyl ring, an optionally substituted monocyclic cycloalkenyl ring or an optionally substituted monocyclic aryl ring, or may be absent; or (ii) ring Y, together with the carbon atoms to which it is attached, form an optionally substituted phenyl ring; and ring Z, together with two ring atoms of ring Y, form an optionally substituted monocyclic heterocyclic ring or an optionally substituted monocyclic heteroaryl ring, wherein said monocyclic heterocyclic or heteroaryl ring comprises at least one N ring atom; and wherein ring X, together with the carbon atoms to which it is attached, form:

(a) an optionally substituted monocyclic heterocyclic ring, an optionally substituted monocyclic heteroaryl ring, an optionally substituted fused bicyclic heterocyclic ring or an optionally substituted fused bicyclic heteroaryl ring; or (b) a phenyl ring substituted by a heterocyclic or heteroaryl ring, wherein said phenyl, heterocyclic and/or heteroaryl ring are optionally substituted;

$R_4$ is selected from the group consisting of sulfonamide, urea and $NHC(O)R_{17}$ wherein $R_{17}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_3$-$C_6$ cycloalkenyl, all of which may be optionally substituted; and $R_6$, $R_7$ and Rs are independently selected from the group consisting of H, OH, protected OH, $R_{19}$, O-$R_{19}$, $NR_{18}R_{18}'$, —$C(O)R_{18}$, —$C(S)R_{18}$, —$OC(O)R_{18}$, —$C(O)OR_{18}$, —$NH(C{=}O)R_{18}$, —$C({=}O\ )NR_{18}'$, and $S(O)_nR_{18}$, wherein n=0-2 and each $R_{18}$ and $R_{18}'$ are independently selected from hydrogen, $R_{19}$ and optionally substituted $C_1$-$C_9$ alkanoyl; wherein each $R_{19}$ is independently selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, cycloalkyl, cycloalkenyl, heteroaryl and heterocyclyl, wherein any $R_{19}$ group is optionally substituted;

wherein the compound of Formula (I) is not:

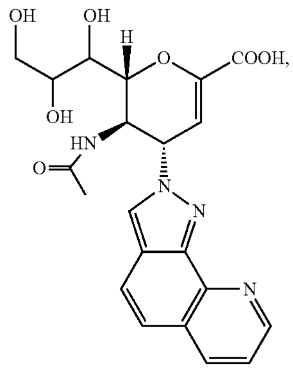

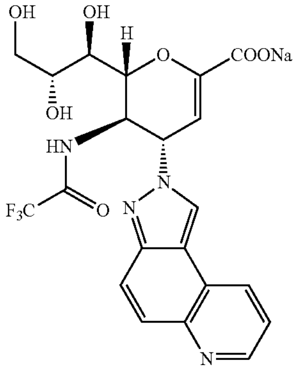

or

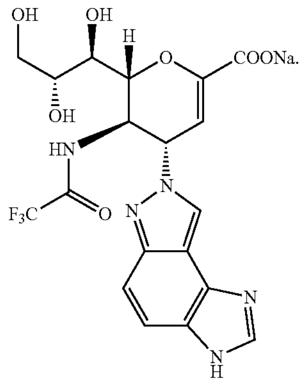

2. The compound of claim 1, wherein the compound of formula (I) is a compound of formula (III):

Formula (III)

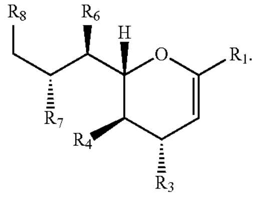

3. The compound of claim 1, wherein $R_3$ is selected from the group consisting of:

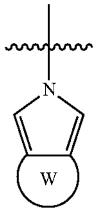
,
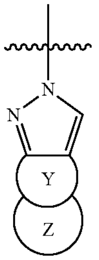
and
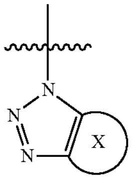

wherein ring W, together with the carbon atoms to which it is attached, form an optionally substituted monocyclic heterocyclic ring, an optionally substituted monocyclic heteroaryl ring, an optionally substituted fused bicyclic heterocyclic ring or an optionally substituted fused bicyclic heteroaryl ring;

wherein ring Y, together with the carbon atoms to which it is attached, form an optionally substituted monocyclic heterocyclic ring or an optionally substituted monocyclic heteroaryl ring; and ring Z, together with two ring atoms of ring Y, form an optionally substituted monocyclic heterocyclic ring, an optionally substituted monocyclic heteroaryl ring, an optionally substituted monocyclic cycloalkyl ring, an optionally substituted monocyclic cycloalkenyl ring or an optionally substituted monocyclic aryl ring, or may be absent; or wherein ring X, together with the carbon atoms to which it is attached, form an optionally substituted monocyclic heterocyclic ring, an optionally substituted monocyclic heteroaryl ring, an optionally substituted fused bicyclic heterocyclic ring or an optionally substituted fused bicyclic heteroaryl ring.

4. A compound of formula (I), or a pharmaceutically acceptable salt thereof:

Formula (I)

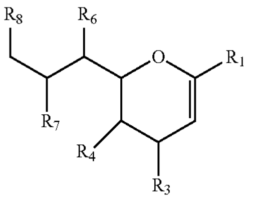

wherein $R_1$ is selected from the group consisting of COOH, or a salt thereof, $C(O)NR_9R_{10}$, and $C(O)OR_{11}$ wherein $R_9$,$R_{10}$ and $R_{11}$ are independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heterosryl and optionally substituted heterocyclyl;

$R_3$ is selected from the group consisting of:

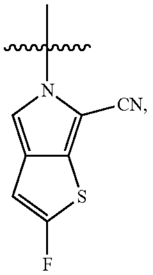
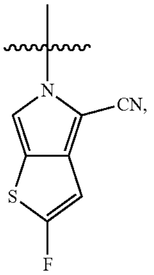
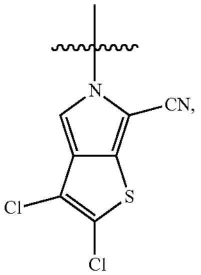
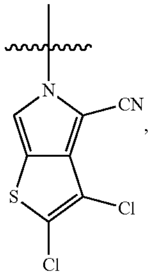
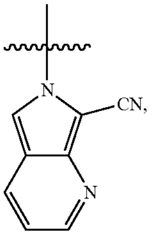
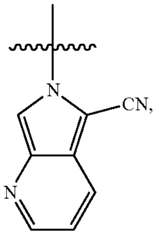
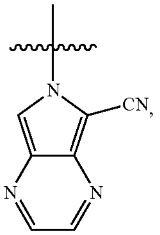
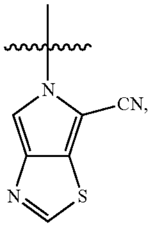
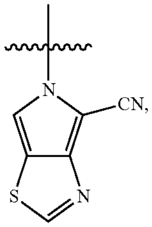
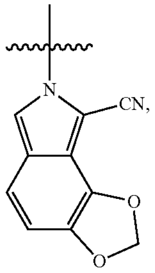
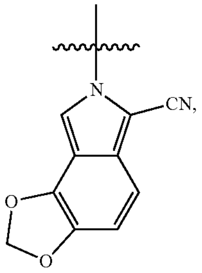
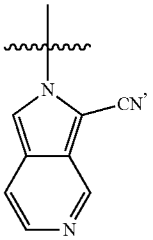
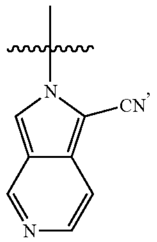
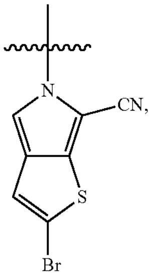
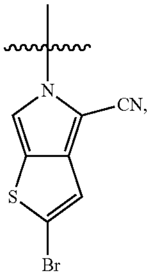
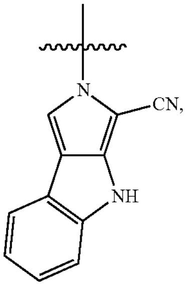
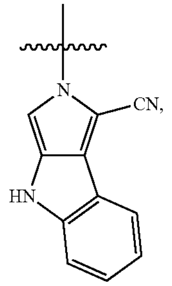
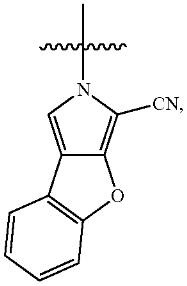

-continued
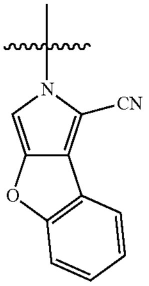
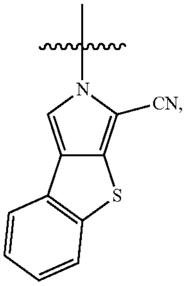
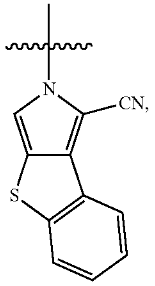
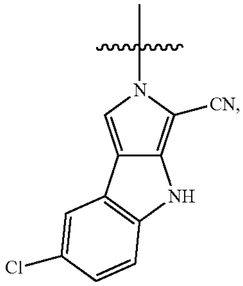
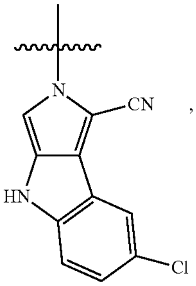
,
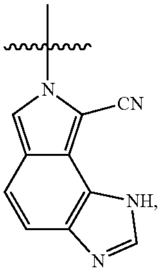
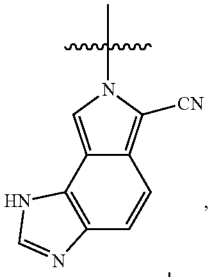
,
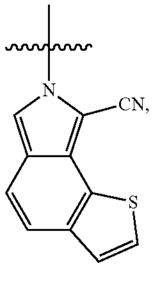
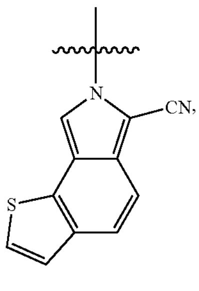
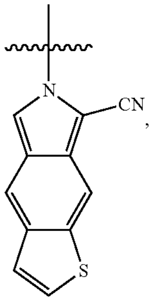
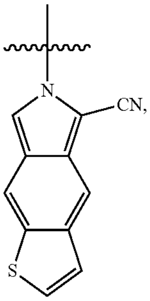
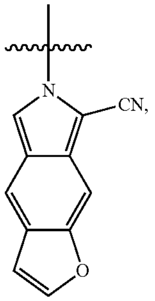
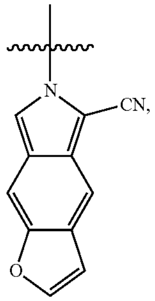
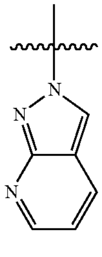
,
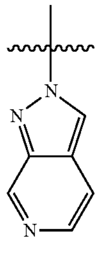
,
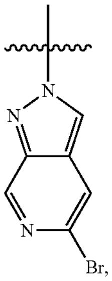
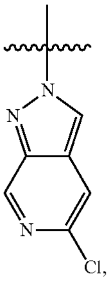
-continued
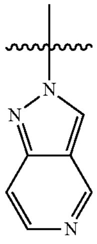
,
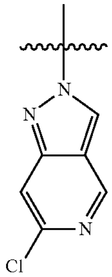
,
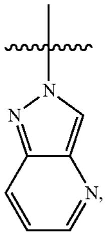
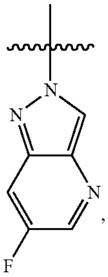
,
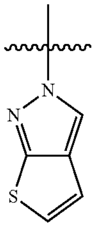
,
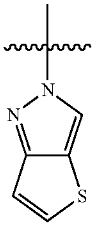
,
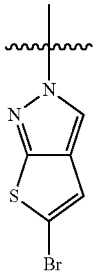
,
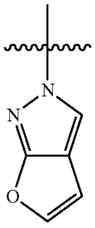
,
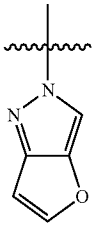
,
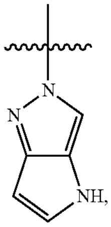
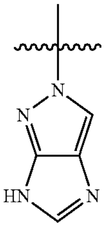
,
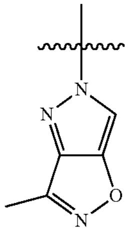
,
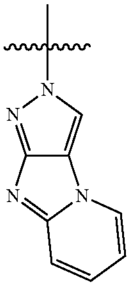
,
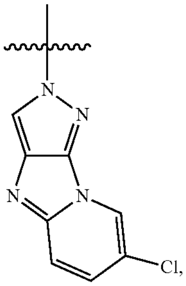
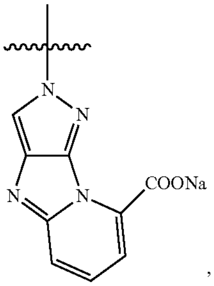
,
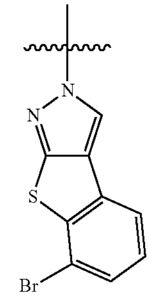
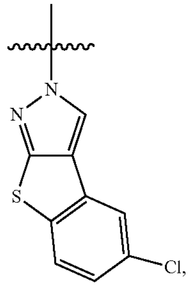
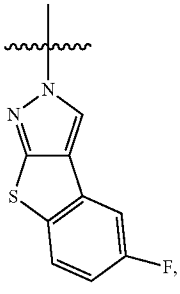
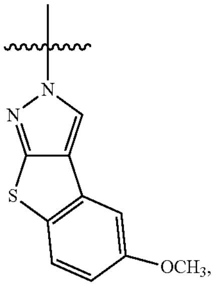
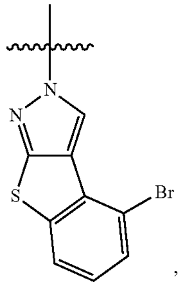
,
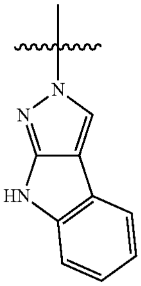
, -continued

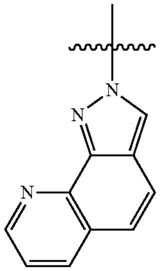, 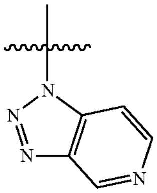, 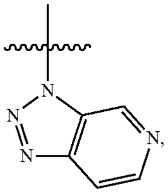

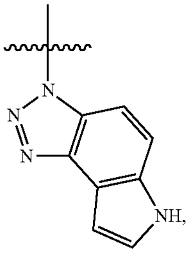 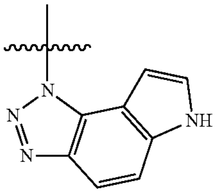 and

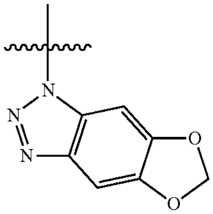 ;

$R_4$ is selected from the group consisting of sulfonamide, urea, and $NHC(O)R_{17}$ wherein $R_{17}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_3$-$C_6$ cycloalkenyl, all of which may be optionally substituted; and $R_6$, $R_7$ and $R_8$ are independently selected from the group consisting of H, OH, protected OH, $R_{19}$, O—$R_{19}$, $NR_{18}R_{18}'$, —$C(O)R_{18}$, —$C(S)R_{18}$, —$OC(O)R_{18}$, —$C(O)OR_{18}$, —$NH(C{=}O)R_{18}$, —$C({=}O)NR_{18}R_{18}'$, and $S(O)_nR_{18}$, wherein n=0-2 and each $R_{18}$ and $R_{18}'$ are independently selected from hydrogen, $R_{19}$ and optionally substituted $C_1$-$C_9$ alkanoyl; wherein each $R_{19}$ is independently selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, cycloalkyl, cycloalkenyl, heteroaryl and heterocyclyl, wherein any $R_{19}$ group is optionally substituted;

wherein the compound of Formula (I) is not:

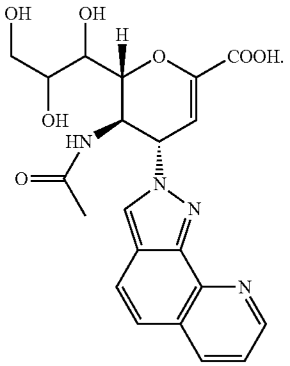 [SMILES: CC(=O)N[C@H]1[C@H](C(O)C(O)CO)OC(C(=O)O)=C[C@@H]1n1cc2ccc3cccnc3c2n1]

5. The compound of claim 4, wherein $R_3$ is selected from the group consisting of:

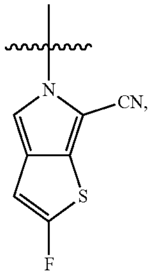 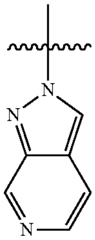, 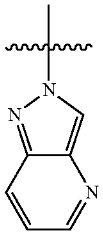,

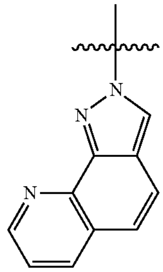, 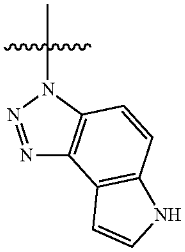 and

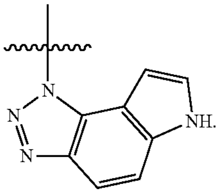

6. The compound of claim 1, wherein $R_1$ is COOH, or a salt thereof, or $C(O)OR_{11}$ wherein Ru is selected from methyl, ethyl and propyl.

7. The compound of claim 1, wherein $R_4$ is selected from the group consisting of:

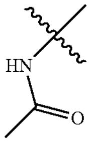, 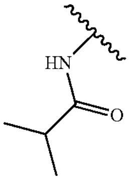, 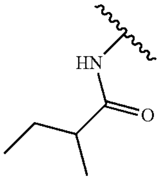,

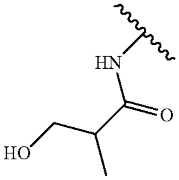, 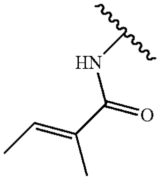, 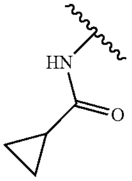,

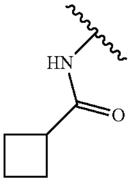, 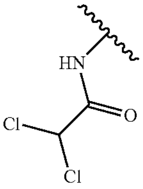, 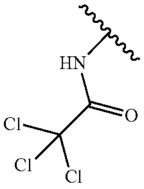,

-continued
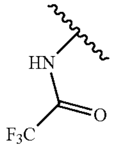, 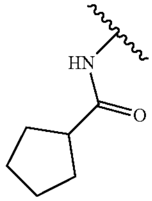, 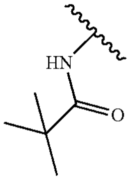,
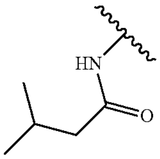, 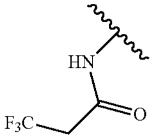, 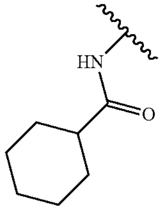,
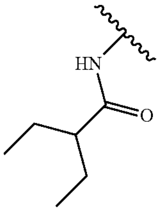, 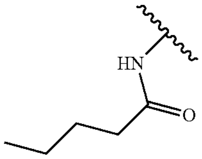,
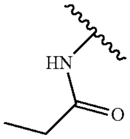, 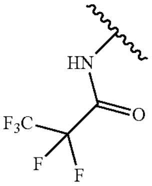, 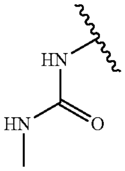,
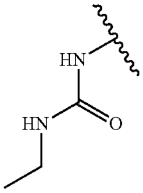, 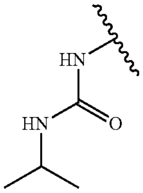, 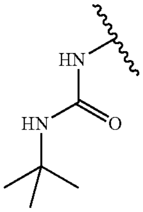,
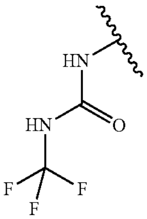, 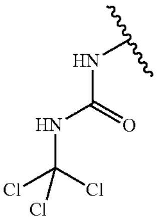, 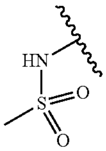,
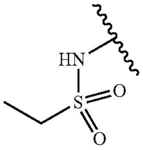, 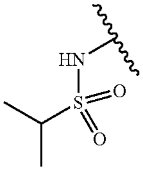, 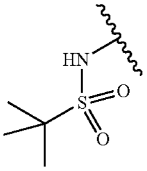,
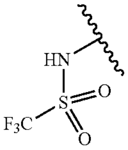, 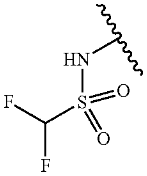, 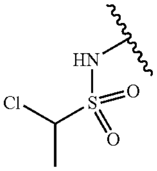,
-continued
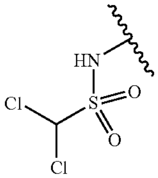 and 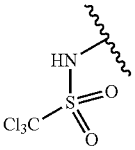.
8. The compound of claim 1, wherein $R_4$ is selected from the group consisting of —$NHC(O)CH_3$, —$NHC(O)CH(CH_3)_2$, —$NHC(O)CF_3$ and —$NHC(O)CH_2CH_3$.
9. The compound of claim 1, wherein $R_6$, $R_7$ and $R_8$ are independently selected from OH and —$OC(O)CH_3$.
10. The compound of claim 4, wherein the compound of formula (I) is a compound selected from the group consisting of:
IE1993-40
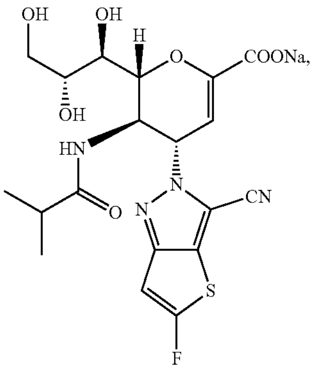
JC2001-48
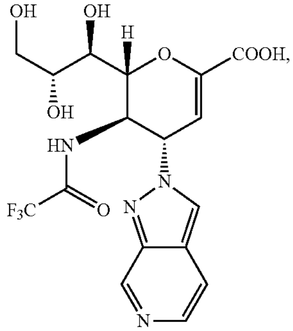
JC2001-49
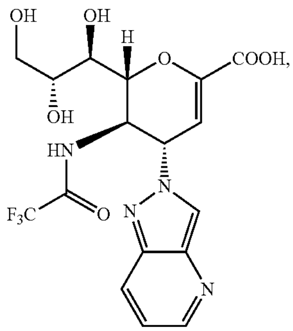

-continued

RP1967-89

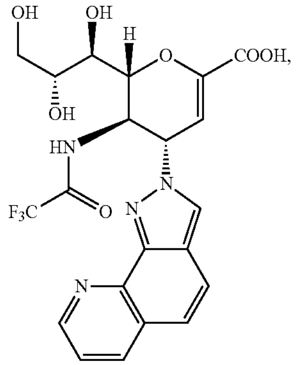

IE1963-113a

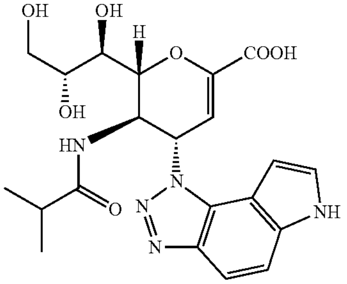

and

IE1963-113b

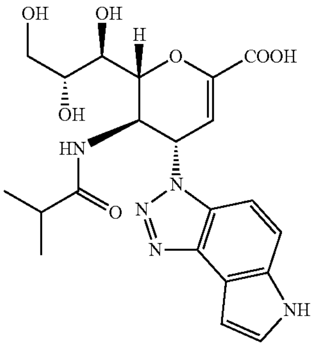

or a pharmaceutically acceptable salt thereof and protected forms thereof and analogues thereof.

11. A compound of formula (I), or a pharmaceutically acceptable salt thereof:

Formula (I)

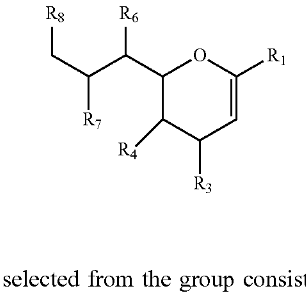

wherein $R_1$ is selected from the group consisting of COOH, or a salt thereof, $C(O)NR_9R_{10}$, and $C(O)OR_{11}$ wherein $R_9$, $R_{10}$ and $R_{11}$ are independently selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted aryl, optionally substituted heteroaryl and optionally substituted heterocyclyl;

$R_3$ is selected from the group consisting of:

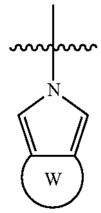

,

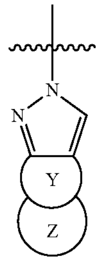

and

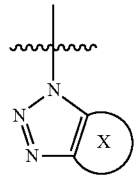

wherein ring W, together with the carbon atoms to which it is attached, form an optionally substituted monocyclic heterocyclic ring, an optionally substituted monocyclic heteroaryl ring, an optionally substituted fused bicyclic heterocyclic ring or an optionally substituted fused bicyclic heteroaryl ring;

wherein:

(i) ring Y, together with the carbon atoms to which it is attached, form an optionally substituted monocyclic heterocyclic ring or an optionally substituted monocyclic heteroaryl ring; and ring Z, together with two ring atoms of ring Y, form an optionally substituted monocyclic heterocyclic ring, an optionally substituted monocyclic heteroaryl ring, an optionally substituted monocyclic cycloalkyl ring, an optionally substituted monocyclic cycloalkenyl ring or an optionally substituted monocyclic aryl ring, or may be absent; or (ii) ring Y, together with the carbon atoms to which it is attached, form an optionally substituted phenyl ring; and ring Z, together with two ring atoms of ring Y, form an optionally substituted monocyclic heterocyclic ring or an optionally substituted monocyclic heteroaryl ring, wherein said monocyclic heterocyclic or heteroaryl ring comprises at least one N ring atom; and wherein ring X, together with the carbon atoms to which it is attached, form:

(a) an optionally substituted monocyclic heterocyclic ring, an optionally substituted monocyclic heteroaryl ring, an optionally substituted fused bicyclic heterocyclic ring or an optionally substituted fused bicyclic heteroaryl ring; or (b) a phenyl ring substituted by a heterocyclic or heteroaryl ring, wherein said phenyl, heterocyclic and/or heteroaryl ring are optionally substituted;

$R_4$ is selected from the group consisting of sulfonamide, urea and $NHC(O)R_{17}$ wherein $R_{17}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_3$-$C_6$ cycloalkenyl, all of which may be optionally substituted; and $R_6$, $R_7$ and $R_8$ are independently selected from the group consisting of H, OH, protected OH, $R_{19}$, O—$R_{19}$, $NR_{18}R_{18}'$, —$C(O)R_{18}$, —$C(S)R_{18}$, —$OC(O)R_{18}$, —$C(O)OR_{18}$, —$NH(C{=}O)R_{18}$, —$C({=}O)NR_{18}R_{18}'$, and $S(O)_nR_{18}$, wherein n=0-2 and each $R_{18}$ and $R_{18}'$ are independently selected from hydrogen, $R_{19}$ and optionally substituted $C_1$-$C_9$ alkanoyl; wherein each $R_{19}$ is independently selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, cycloalkyl, cycloalkenyl, heteroaryl and heterocyclyl, wherein any $R_{19}$ group is optionally substituted.

12. A pharmaceutical composition comprising an effective amount of a compound of claim 1, or a pharmaceutically acceptable salt thereof, and a pharmaceutically acceptable carrier, diluent and/or excipient.

13. The compound of claim 4, wherein the compound of formula (I) is a compound of formula (III):

Formula (III)

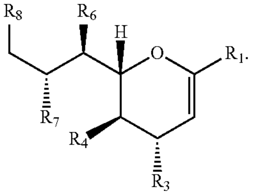

14. The compound of claim 4, wherein $R_1$ is COOH, or a salt thereof, or $C(O)OR_{11}$ wherein $R_{11}$ is selected from methyl, ethyl and propyl.

15. The compound of claim 4, wherein R4 is selected from the group consisting of:

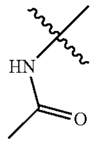 , 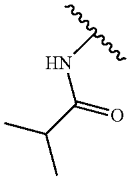 , 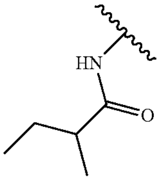 ,

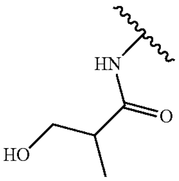 , 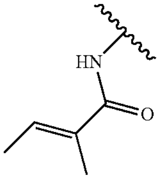 , 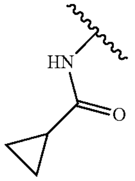 ,

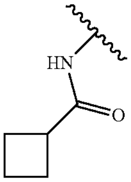 , 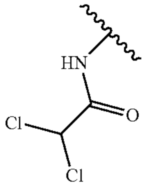 , 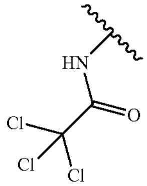 ,

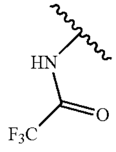 , 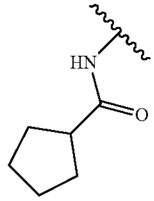 , 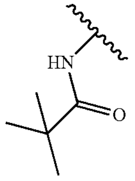 ,

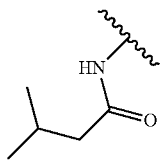 , 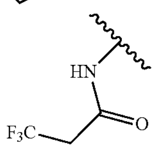 , 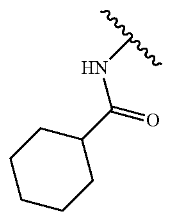 ,

-continued

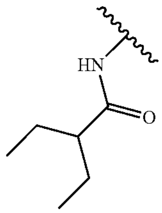 , 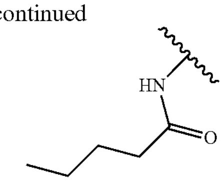 ,

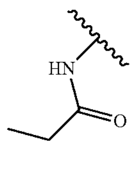 , 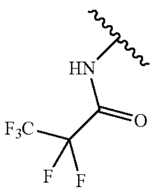 , 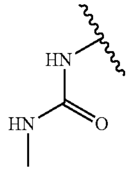 ,

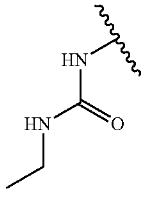 , 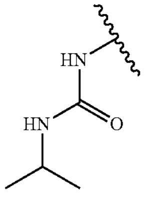 , 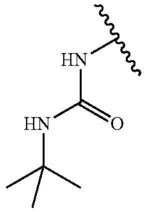 ,

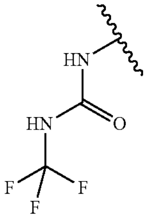 , 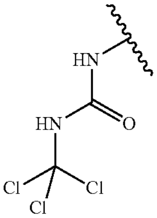 , 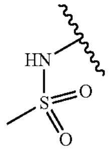 ,

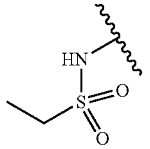 , 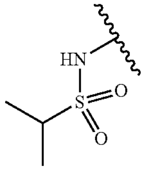 , 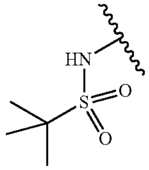 ,

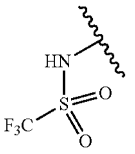 , 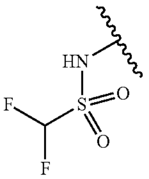 , 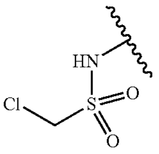 ,

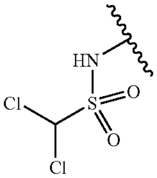 and 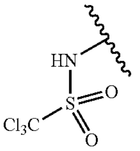 .

16. The compound of claim 4, wherein $R_4$ is selected from the group consisting of —$NHC(O)CH_3$, —$NHC(O)CH(CH_3)_2$, —$NHC(O)CF_3$ and —$NHC(O)CH_2CH_3$.

17. The compound of claim 4, wherein $R_6$, $R_7$ and $R_8$ are independently selected from OH and —$OC(O)CH_3$.

18. A pharmaceutical composition comprising an effective amount of a compound of claim 4, or a pharmaceutically acceptable salt thereof, and a pharmaceutically acceptable carrier, diluent and/or excipient.

19. The compound of claim 1, wherein $R_1$ is selected from the group consisting of COOH, or a salt thereof, $C(O)NR_9R_{10}$, and $C(O)OR_{11}$ wherein $R_9$, $R_{10}$ and $R^{11}$ are independently selected from the group consisting of hydrogen, $C_1$-$C_6$ alkyl, $C_2$-$C_6$ alkenyl, $C_2$-$C_6$ alkynyl, aryl, and heterocyclyl; wherein said $C_1$-$C_6$ alkyl, $C_2$-$C_6$ alkenyl, $C_2$-$C_6$ alkynyl, aryl, heteroaryl and heterocyclyl are optionally substituted by one or more $R_{50}$; wherein $R_{50}$ is selected from the group consisting of $R_{53}$, —O—$R_{53}$, —S—$R_{53}$, —C(O)—$R_{53}$, —C(S)—$R_{53}$, —C(O)—O—$R_{53}$, —O—C(O)—$R_{53}$, —O—C(S)—$R_{53}$, —C(S)—O—$R_{53}$, CN, OH, oxo, $NR_{51}R_{51}'$, Cl, F, Br, I, aryl optionally substituted by at least one $R_{52}$ and heterocyclyl optionally substituted by at least one $R_{52}$; wherein $R_{51}$ and $R_{51}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$-$C_1$-$C_9$ alkyl and C↑O—NH—$C_1$-$C_9$ alkyl; wherein $R_{52}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{51}R_{51}'$, Cl, F, Br and I; and wherein $R_{53}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl;

$R_3$ is selected from the group consisting of:

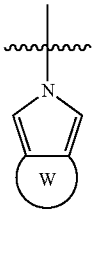
,
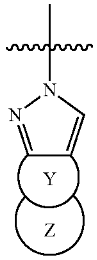
and
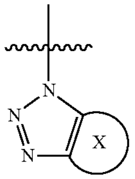

wherein ring W, together with the carbon atoms to which it is attached, form a monocyclic heterocyclic ring optionally substituted by one or more $R_{55}$, a monocyclic heteroaryl ring optionally substituted by one or more $R_{55}$, a fused bicyclic heterocyclic ring optionally substituted by one or more $R_{55}$, or a fused bicyclic heteroaryl ring optionally substituted by one or more $R_{55}$; wherein $R_{55}$ is selected from the group consisting of $R_{58}$, —O—$R_{58}$, —S—$R_{58}$, —C(O)—$R_{58}$, —C(S)—$R_{58}$, —C(O)—O—$R_{58}$, —O—C(O)—$R_{58}$, —O—C(S)—$R_{58}$, —C(S)—O—$R_{58}$, CN, OH, oxo, $NR_{56}R_{56}'$, Cl, F, Br, I, aryl optionally substituted by at least one $R_{57}$ and heterocyclyl optionally substituted by at least one $R_{57}$, wherein $R_{56}$ and $R_{56}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, aryl, $SO_2$-$C_1$-$C_9$ alkyl and C—O—NH—$C_1$-$C_9$ alkyl; wherein $R_{57}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{56}R_{56}'$, Cl, F, Br and I; and wherein $R_{58}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, heteroaryl, heterocyclyl, cycloalkyl and cycloalkenyl;

wherein:

(i) ring Y, together with the carbon atoms to which it is attached, form a monocyclic heterocyclic ring optionally substituted by one or more $R_{60}$ or a monocyclic heteroaryl ring optionally substituted by one or more $R_{60}$; and ring Z, together with two ring atoms of ring Y, form a monocyclic heterocyclic ring optionally substituted by one or more $R_{60}$, a monocyclic heteroaryl ring optionally substituted by one or more $R_{60}$, a monocyclic cycloalkyl ring optionally substituted by one or more $R_{60}$, a monocyclic cycloalkenyl ring optionally substituted by one or more $R_{60}$ or a monocyclic aryl ring optionally substituted by one or more $R_{60}$, or may be absent;

wherein $R_{60}$ is selected from the group consisting of $R_{63}$, —O—$R_{63}$, —S—$R_{63}$, —C(O)—$R_{63}$, —C(S)—$R_{63}$, —C(O)—O—$R_{63}$, —C(O)—OH (or a salt thereof), —O—C(O)—$R_{63}$, —O—C(S)—$R_{63}$, —C(S)—O—$R_{63}$, CN, OH, oxo, $NR_{61}R_{61}'$, Cl, F, Br, I, aryl optionally substituted by at least one $R_{62}$ and heterocyclyl optionally substituted by at least one $R_{62}$; wherein $R_{61}$ and $R_{61}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, aryl, $SO_2$-$C_1$-$C_9$ alkyl and C═O—NH—$C_1$-$C_9$ alkyl; wherein $R_{62}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{61}R_{61}'$, Cl, F, Br and I; and wherein $R_{63}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, heteroaryl, heterocyclyl, cycloalkyl and cycloalkenyl; or (ii) ring Y, together with the carbon atoms to which it is attached, form a phenyl ring optionally substituted by one or more $R_{65}$; and ring Z, together with two ring atoms of ring Y, form a monocyclic heterocyclic ring optionally substituted by one or more $R_{65}$, or a monocyclic heteroaryl ring optionally substituted by one or more $R_{65}$, wherein said monocyclic heterocyclic or heteroaryl ring comprises at least one N ring atom;

wherein $R_{65}$ is selected from the group consisting of $R_{68}$, —O—$R_{68}$, —S—$R_{68}$, —C(O)—$R_{68}$, —C(S)—$R_{68}$, —C(O)—O—$R_{68}$, —O—C(O)—$R_{68}$, —O—C(S)—$R_{68}$, —C(S)—O—$R_{68}$, CN, OH, oxo, $NR_{66}R_{66}'$, Cl, F, Br, I, aryl optionally substituted by at least one $R_{67}$ and heterocyclyl optionally substituted by at least one $R_{67}$; wherein $R_{66}$ and $R_{66}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, aryl, $SO_2$-$C_1$-$C_9$ alkyl and C═O—NH—$C_1$-$C_9$ alkyl; wherein $R_{67}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{66}R_{66}'$, Cl, F, Br and I; and wherein $R_{68}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, heteroaryl, heterocyclyl, cycloalkyl and cycloalkenyl; and wherein ring X, together with the carbon atoms to which it is attached, form:

(a) a monocyclic heterocyclic ring optionally substituted by one or more $R_{70}$, a monocyclic heteroaryl ring optionally substituted by one or more $R_{70}$, a fused bicyclic heterocyclic ring optionally substituted by one or more $R_{70}$, or a fused bicyclic heteroaryl ring optionally substituted by one or more $R_{70}$; or (b) a phenyl ring substituted by a heterocyclic or heteroaryl ring, wherein said phenyl, heterocyclic and/or heteroaryl ring are optionally substituted by one or more $R_{70}$;

wherein $R_{70}$is selected from the group consisting of $R_{73}$, —O—$R_{73}$, —S—$R_{73}$, —C(O)—$R_{73}$, —C(S)—$R_{73}$, —C(O)—O—$R_{73}$, —O—C(O)—$R_{73}$, —O—C(S)—$R_{73}$, —C(S)—O—$R_{73}$, CN, OH, oxo, $NR_{71}R_{71}'$, Cl, F, Br, I, aryl optionally substituted by at least one $R_{72}$ and heterocyclyl optionally substituted by at least one $R_{72}$; wherein $R_{71}$ and $R_{71}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C—O—$C_1$-$C_9$ alkyl, aryl, $SO_2$-$C_1$-$C_9$ alkyl and C—O—NH—$C_1$-$C_9$ alkyl; wherein $R_{72}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{66}R_{66}'$, Cl, F, Br and I; and wherein $R_{73}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, heteroaryl, heterocyclyl, cycloalkyl and cycloalkenyl;

$R_4$ is selected from the group consisting of sulfonamide, urea and $NHC(O)R_{17}$ wherein $R_{17}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_3$-$C_6$ cycloalkenyl; wherein said $R_{17}$ groups may be optionally substituted by one or more $R_{75}$;

wherein $R_{75}$ is selected from the group consisting of $R_{78}$, —O—$R_{78}$, —S—$R_{78}$, —C(O)—$R_{78}$, —C(S)—$R_{78}$, —C(O)—O—$R_{78}$, —O—C(O)—$R_{78}$, —O—C(S)—$R_{78}$, —C(S)—O—$R_{78}$, CN, OH, oxo, $NR_{76}R_{76}'$, Cl, F, Br, I, aryl optionally substituted by at least one $R_{77}$ and heterocyclyl optionally substituted by at least one $R_{77}$, wherein $R_{76}$ and $R_{76}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C—O—$C_1$-$C_9$ alkyl, $SO_2$-$C_1$-$C_9$ alkyl and C═O—NH—$C_1$-$C_9$ alkyl; wherein $R_{77}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{76}R_{76}'$, Cl, F, Br and I; and wherein $R_{78}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl; and $R_6$, $R_7$ and $R_8$ are independently selected from the group consisting of H, OH, protected OH, $R_{19}$, O—$R_{19}$, $NR_{18}R_{18}'$, —$C(O)R_{18}$, —$C(S)R_{18}$, —$OC(O)R_{18}$, —$C(O)OR_{18}$, —$NH(CO)R_{18}$, —C(═O)$NR_{18}R_{18}'$, and $S(O)_nR_{18}$, wherein n=0-2 and each $R_{18}$ and $R_{18}'$ are independently selected from hydrogen, $R_{19}$ optionally substituted by one or more $R_{80}$ and $C_1$-$C_9$ alkanoyl optionally substituted by one or more $R_{80}$; wherein each $R_{19}$ is independently selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, cycloalkyl, cycloalkenyl, heteroaryl and heterocyclyl; wherein $R_{80}$ is selected from the group consisting of $R_{83}$, —O—$R_{83}$, —S—$R_{83}$, —C(O)—$R_{83}$, —C(S)—$R_{83}$, —C(O)—O-$R_{83}$, —O—C(O)—$R_{83}$, —O—C(S)—$R_{83}$, —C(S)—O-$R_{83}$, CN, OH, oxo, $NR_{81}R_{81}'$, Cl, F, Br, I, aryl optionally substituted by at least one $R_{82}$ and heterocyclyl optionally substituted by at least one $R_{82}$; wherein $R_{81}$ and $R_{81}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$-$C_1$-$C_9$ alkyl and C—O—NH—$C_1$-$C_9$ alkyl; wherein $R_{82}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{76}R_{76}'$, Cl, F, Br and I; and wherein $R_{83}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl.

20. The compound of claim 4, wherein $R_1$ is selected from the group consisting of COOH, or a salt thereof, $C(O)NR_9R_{10}$, and $C(O)OR_{11}$ wherein $R_9$, $R_{10}$ and $R^{11}$ are independently selected from the group consisting of hydrogen, $C_1$-$C_6$ alkyl, $C_2$-$C_6$ alkenyl, $C_2$-$C_6$ alkynyl, aryl, and heterocyclyl; wherein said $C_1$-$C_6$ alkyl, $C_2$-$C_6$ alkenyl, $C_2$-$C_6$ alkynyl, aryl, heteroaryl and heterocyclyl are optionally substituted by one or more $R_{50}$; wherein $R_{50}$ is selected from the group consisting of $R_{53}$, —O—$R_{53}$, —S—$R_{53}$, —C(O)—$R_{53}$, —C(S)—$R_{53}$, —C(O)—O—$R_{53}$, —O—C(O)—$R_{53}$, —O—C(S)—$R_{53}$, —C(S)—O—$R_{53}$, CN, OH, oxo, $NR_{51}R_{51}'$, Cl, F, Br, I, aryl optionally substituted by at least one $R_{52}$ and heterocyclyl optionally substituted by at least one $R_{52}$; wherein $R_{51}$ and $R_{51}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$-$C_1$-$C_9$ alkyl and C↑O—NH—$C_1$-$C_9$ alkyl; wherein $R_{52}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{51}R_{51}'$, Cl, F, Br and I; and wherein $R_{53}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl;

$R_4$ is selected from the group consisting of sulfonamide, urea and $NHC(O)R_{17}$ wherein $R_{17}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, and $C_3$-$C_6$ cycloalkenyl; wherein said $R_{17}$ groups may be optionally substituted by one or more $R_{75}$; wherein $R_{75}$ is selected from the group consisting of $R_{78}$, —O—$R_{78}$, —S—$R_{78}$, —C(O)—$R_{78}$, —C(S)—$R_{78}$, —C(O)—O—$R_{78}$, —O—C(O)—$R_{78}$, —O—C(S)—$R_{78}$, —C(S)—O—$R_{78}$, CN, OH, oxo, $NR_{76}R_{76}'$, Cl, F, Br, I, aryl optionally substituted by at least one $R_{77}$ and heterocyclyl optionally substituted by at least one $R_{77}$, wherein $R_{76}$ and $R_{76}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C—O—$C_1$-$C_9$ alkyl, $SO_2$-$C_1$-$C_9$ alkyl and C═O—NH—$C_1$-$C_9$ alkyl; wherein $R_{77}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{76}R_{76}'$, Cl, F, Br and I; and wherein $R_{78}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl; and $R_6$, $R_7$ and $R_8$ are independently selected from the group consisting of H, OH, protected OH, $R_{19}$, O—$R_{19}$, $NR_{18}R_{18}'$, —$C(O)R_{18}$, —$C(S)R_{18}$, —$OC(O)R_{18}$, —$C(O)OR_{18}$, —$NH(CO)R_{18}$, —C(═O)$NR_{18}R_{18}'$, and $S(O)_nR_{18}$, wherein n=0-2 and each $R_{18}$ and $R_{18}'$ are independently selected from hydrogen, $R_{19}$ optionally substituted by one or more $R_{80}$ and $C_1$-$C_9$ alkanoyl optionally substituted by one or more $R_{80}$; wherein each $R_{19}$ is independently selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, aryl, cycloalkyl, cycloalkenyl, heteroaryl and heterocyclyl; wherein $R_{80}$ is selected from the group consisting of $R_{83}$, —O—$R_{83}$, —S—$R_{83}$, —C(O)—$R_{83}$, —C(S)—$R_{83}$, —C(O)—O-$R_{83}$, —O—C(O)—$R_{83}$, —O—C(S)—$R_{83}$, —C(S)—O-$R_{83}$, CN, OH, oxo, $NR_{81}R_{81}'$, Cl, F, Br, I, aryl optionally substituted by at least one $R_{82}$ and heterocyclyl optionally substituted by at least one $R_{82}$; wherein $R_{81}$ and $R_{81}'$ are independently selected from hydrogen, $C_1$-$C_9$ alkyl, $C_1$-$C_9$ haloalkyl, $C_2$-$C_9$ alkenyl, $C_2$-$C_9$ haloalkenyl, $C_2$-$C_9$ alkynyl, $C_2$-$C_9$ haloalkynyl, C═O—$C_1$-$C_9$ alkyl, $SO_2$-$C_1$-$C_9$ alkyl and C—O—NH—$C_1$-$C_9$ alkyl; wherein $R_{82}$ is selected from the group consisting of $C_1$-$C_6$ alkyl, $C_1$-$C_6$ haloalkyl, $C_1$-$C_6$ alkoxy, $C_1$-$C_6$ haloalkoxy, CN, OH, oxo, $NR_{76}R_{76}'$, Cl, F, Br and I; and wherein $R_{83}$ is selected from the group consisting of $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, and $C_2$-$C_6$ haloalkynyl.

21. The compound of claim 4, wherein the compound of formula (I) is a compound selected from the group consisting of:

IE1993-40

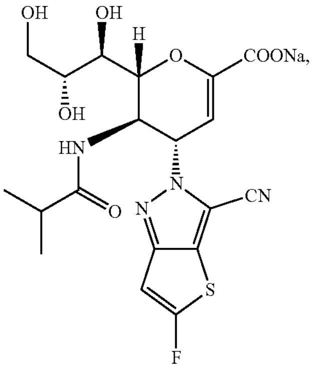

JC2001-48

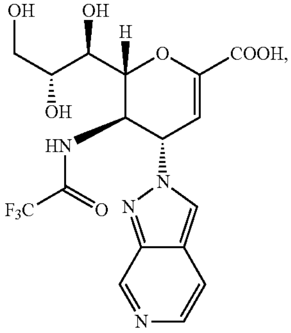

-continued

JC2001-49

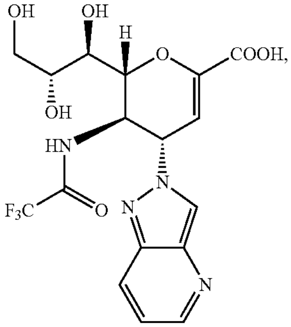

RP1967-89

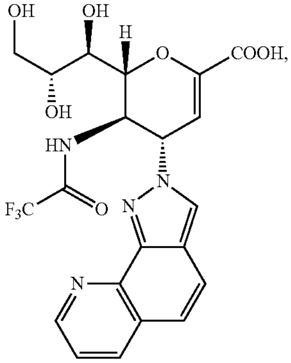

IE1963-113a

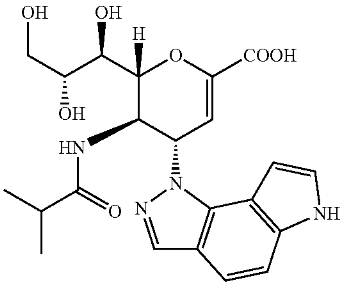

and

IE1963-113b

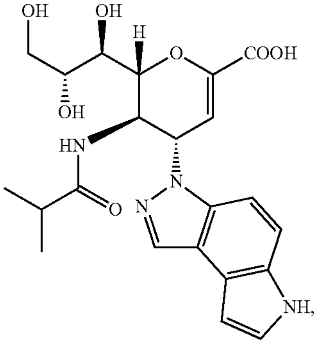

or a pharmaceutically acceptable salt thereof.

* * * * *